(12) United States Patent
Potyrailo

(10) Patent No.: US 6,567,753 B2
(45) Date of Patent: May 20, 2003

(54) DEVICES AND METHODS FOR SIMULTANEOUS MEASUREMENT OF TRANSMISSION OF VAPORS THROUGH A PLURALITY OF SHEET MATERIALS

(75) Inventor: Radislav Alexandrovich Potyrailo, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/681,433

(22) Filed: Apr. 4, 2001

(65) Prior Publication Data

US 2002/0173922 A1 Nov. 21, 2002

(51) Int. Cl.[7] ................................................. G01H 1/00
(52) U.S. Cl. ....................................................... 702/39
(58) Field of Search ........................... 702/39; 73/24.02, 73/53.01; 350/96; 356/36, 450; 428/332; 86/36.02; 364/497

(56) References Cited

U.S. PATENT DOCUMENTS

| | | | |
|---|---|---|---|
| 4,673,299 A | 6/1987 | Dakin | 374/131 |
| 4,847,783 A * | 7/1989 | Grace et al. | 422/98 |
| 5,106,938 A | 4/1992 | Bookbinder et al. | 528/176 |
| 5,233,194 A | 8/1993 | Mauze et al. | 250/341.2 |
| 5,237,631 A | 8/1993 | Gavish et al. | 385/12 |
| 5,356,668 A | 10/1994 | Paton et al. | 427/2.25 |
| 5,451,632 A | 9/1995 | Okumura et al. | 525/92 A |
| 5,488,086 A | 1/1996 | Umeda et al. | 525/478 |
| 5,519,096 A | 5/1996 | Hara | 250/343 |
| 5,528,040 A | 6/1996 | Lehmann | 528/196 |
| 5,644,017 A | 7/1997 | Drumright et al. | 525/146 |
| 5,674,943 A | 10/1997 | Farah et al. | 422/82.07 |
| 5,708,957 A | 1/1998 | Chuang et al. | 528/196 |
| 5,717,056 A | 2/1998 | Varadarajan et al. | 250/227.16 |
| 5,744,794 A | 4/1998 | Michie et al. | 524/537 |
| 5,886,249 A * | 3/1999 | Bonne et al. | 73/24.02 |
| 5,919,526 A | 7/1999 | Eckberg et al. | 427/387 |
| 5,919,886 A | 7/1999 | Matsuda et al. | 528/42 |
| 5,969,066 A | 10/1999 | Enokida et al. | 526/247 |
| 5,973,068 A | 10/1999 | Yamaya et al. | 524/805 |
| 5,973,126 A | 10/1999 | Ueno et al. | 534/656 |
| 5,981,008 A | 11/1999 | Hofmann | 428/35.7 |
| 5,981,073 A | 11/1999 | Pickett et al. | 428/412 |
| 5,990,188 A | 11/1999 | Patel et al. | 522/28 |
| 6,010,616 A | 1/2000 | Lewis et al. | 205/787 |
| 6,034,775 A | 3/2000 | McFarland et al. | 356/364 |
| 6,087,181 A | 7/2000 | Cong | 436/37 |
| 6,093,308 A | 7/2000 | Lewis et al. | 205/787 |
| 6,151,123 A | 11/2000 | Nielsen | 356/445 |
| 6,157,449 A | 12/2000 | Hajduk | 356/367 |
| 6,182,499 B1 | 2/2001 | McFarland et al. | 73/24.06 |
| 6,278,523 B1 * | 8/2001 | Gorecki | 356/450 |

FOREIGN PATENT DOCUMENTS

| | | |
|---|---|---|
| GB | 2156513 A | 10/1985 |
| WO | WO 00/36410 | 6/2000 |

OTHER PUBLICATIONS

Bacon, J.R.; Demas, J.N., "Determination of Oxygen Concentrations by Luminescence Quenching of a Polymer–Immobilized Transition–Metal Complex",*Anal. Chem.* 1987, 59, 2780–2785.

(List continued on next page.)

*Primary Examiner*—John Barlow
*Assistant Examiner*—Tung S Lau
(74) *Attorney, Agent, or Firm*—Noreen C. Johnson; Christian G. Cabou

(57) ABSTRACT

Methods and devices are disclosed for determining barrier properties of at least one barrier coating with respect to a plurality of fluids. These methods and systems include a combination of acoustic wave and optical detection measurements. A dual-response acoustic wave transducer coated with the barrier coating is exposed to one or more of the fluids. The effects on the barrier coating, such as permeation of the fluid or dissolution of the coating, are measured using acoustic wave and optical techniques and the corresponding barrier properties are determined with respect to the fluids.

61 Claims, 15 Drawing Sheets

LEGEND: 12 – Transducer, 13 – Planar Waveguide Transducer, 18 – Sensing Material, 20 – Barrier Coating, 28 – Fluids

OTHER PUBLICATIONS

Berndt, K.W.; Lakowicz, J.R., "Electroluminescent Lamp-based Phase Fluorometer and Oxygen Sensor", *Anal. Biochem.* 1992, 201, 319–325.

Amao, Y.; Asai, K.; Okura, I.; Shinohara, H.; Nishide, J., "Platinum Porphyrin Embedded in Poly(1–Trimthylsilyl–1–Propyne) Film as an Optical Sensor for Trace Analysis of Oxygen", *Analyst 2000*, 125, 1911–1914.

Potyrailo, R.A.; Hieftje, G.M., "Oxygen Detection by Fluorescence Quenching of Tetraphenylporphyrin Immobilized in the Original Cladding of an Optical Fiber",*Anal Chim. Acta* 1998, 370, 1–8.

Potyrailo, R.A.; Hieftje, G.M., "Use of the Original Silicone Cladding of an Optical Fiber as a Reagent Immobilization Medium for Intrinsic Chemical Sensors", *Fresenius' J. Anal. Chem.* 1999, 364, 32–40.

Wolfbeis, O.S., "Fiber Optic Chemical Sensors and Biosensors", O.S. Wolfbeis, Ed.; CRC Press: Boca Raton, FL, 1991; vol. 2; pp. 19–53.

Hartmann, P.; Trettnak, W., "Effects of Polymer Matrices on Calibration Functions of Luminescent Oxygen Sensors Based on Porphyrin Ketone Complexes",*Anal. Chem.* 1996, 68, 2615–2620.

Berlman, I.B., "Handbook of Fluorescence Spectra of Aromatic Molecules", Academic Press, New York, NY, 1971.

Hobbs, S.E.; Potyrailo, R.A.; Hieftje, G.M., "Scintillator Light Source for Chemical Sensing in the Near Ultraviolet", *Anal. Chem.* 1997, 69, 3375–3379.

Demas, J.N.; DeGraff, B.A.; Coleman, P.B., "Oxygen Sensors Based on Luminescence Quenching",*Anal. Chem.* 1999, 71, 793A–800A.

Demas, J.N.; DeGraff, B.A., "Design and Applications of Highly Luminescent Transition Metal Complexes", *Anal. Chem.* 1991, 63, 829A–837A.

Mills, A.; Lepre, A.; Theobald, B.R.; Slade, E.; Murrer, B.A., "Use of Luminescent Gold Compounds in the Design of Thin–Film Oxygen Sensors", *Anal. Chem.* 1997, 69, 2842–2847.

Reichart, C., "Chemical Reviews", 1994, vol. 94, pp. 2319–2358.

Sadaoka, Y.; Matsuguchi, M.; Sakai, Y.; Murata, Y., "Optical Humidity Sensor Using Reichardt's Betain Dye Polymer Composites", *Chem. Lett.* 1992, 53–56.

Sadaoka, Y.; Sakai, Y.; Murata, Y., "Optical Humidity and Ammonia Gas Sensors Using Reichardt's Dye Polymer Composites", Talanta 1992, 39, 1675–1679.

Bacci, M.; Baldini, F.; Bracci, S., "Spectroscopic Behavior of Acid–Base Indicators After Immobilization on Glass Supports", *Appl. Spectrosc.* 1991, 45, 1508–1515.

Sadaoka, Y.; Matsuguchi, M.; Sakai, Y.; Murata, Y., "Optical Humidity Sensing Characteristics of Nafion Dyes Composite Thin Films", *Sens. Actuators B* 1992, 7, 443–446.

Sadaoka, Y.; Sakai, Y.; Murata, Y., "Optical Properties of Cresyl Violet–Polymer Composites for Quantification of Humidity and Ammonia Gas in Ambient Air", *J. Mater. Chem.* 1993, 3, 247–251.

Zinger, B.; Shier, P., "Spectroscopic Studies of Cationic Dyes in Nafion, Preliminary Investigation of a New Sensor for Hydrophilic Contamination in Organic Solvents", *Sens. Actuators B* 1999, 56, 206–214.

Haughland, R.P., "Handbook of Fluorescent Probes and Research Chemicals", Molecular Probes, Eugene, OR, 1996.

Ruch, W.E., "Chemical Detection of Gaseous Pollutants", Ann Arbor Science Publishers: Ann Arbor, MI, 1968.

Ballantine, D.S., Jr.; White, R.M.; Martin, S.J.; Ricco, A.J.; Frye, G.C.; Zellers, E.T.; Wohltjen, H., "Acoustic Wave Sensors: Theory, Design, and Physico–Chemical Applications", Chps. 3 and 6, Academic Press: San Diego, CA, 1997.

Michie, W.C.; Culshaw, B.; Konstantaki, M.; McKenzie, I.; Kelly, S.; Graham, N.B.; Moran, C., "Distributed pH and Water Detection Using Fiber Optic Sensors and Hydrogels", *J. Lightwave Techno.* 1995, 13, 1415–1420.

Bownass, D.C.; Barton, J.S.; Jones, J.D.C., "Serially Multiplexed Point Sensor for the Detection of High Humidity in Passive Optical Networks", *Opt. Lett.* 1997, 22, 346–348.

Stern, S.A.; Krishnakumar, B.; Nadakatti, S.M., "Physical Properties of Polymers Handbook", J.E. Mark, Ed.; AIP Press: New York, 1996; pp. 687–700.

Freud, M.S.; Lewis, N.S., "A Chemically Diverse Conducting Polymer–Based 'Electronic Nose'", *Proc. Natl. Acad. Sci. USA* 1995; 92, 2652–2656.

Albert, K.J.; Lewis, N.S.; Schauer, C.L.; Sotzing, G.A., Stitzel, S.E.; Vaid, T.P.; Walt, D.R., "Cross–Reactive Chemical Sensor Arrays", *Chem. Rev.* 2000, 1000, 2595–2626.

Grate, J.W.; Abraham, M.H.; McGill, R.A., "Handbook of Biosensors and Electronic Noses. Medicine, Food, and the Environment", E. Kress–Rogers, Ed.; CRC Press: Boca Raton, FL, 1997, pp. 593–612.

Grate, J.W.; Abraham, M.H., "Solubility Interactions and the Design of Chemically Selective Sorbent Coatings for Chemical Sensors and Arrays", *Sens. Actuators B* 1991, 3, 85–111.

Product Catalog "3M Power–Core Fiber Products", Specialty Fibers, West Haen, CT.

Ruddy, V.; MacCraith, B.D.;Murphy, J.A., "Evanescent Wave Absorption Spectroscopy Using Multimode Fibers", J. Appl. Phys. 1990, 67, 6070–6074.

Brecht, A.; Burckhardt, R.; Rickert, J.; Stemmler, I.; Schuetz, A.; Fischer, S.; Friedrich, T.; Gauglitz, G.; Goepel, W., "Transducer–Based Approach for Parallel Binding Assays", J. Biomolecular Screening, 1996, 1, 191–201.

Gauglitz, G., "Optical Sensor Arrays Based on Microtiterplate Dimensions", Mikrochim. Acta 1999, 131, 9–17.

Rharbi, Y.; Yekta, A.; Winnik, M.A., "A Method for Measuring Oxygen Diffusion and Oxygen Permeation in Polymer Films Based on Fluorescence Quenching",*Anal. Chem.* 1999, 71, 5045–5053.

Lowry, J.H.; Mendlowitz, J.S.; Subramanian, N.S., "Optical Characteristics of Teflon AF Fluoroplastic Materials", *Opt. Eng.* 1992, 31, 1982–1985.

Buck, W.H.; Resnick, P.R.; "Properties of Amorphous Fluoroploymer Based on 2,2–Bistrifluoromethyl–4,5–Difluoro–1,3–Dioxide", 183$^{nd}$ *Meeting of the Electrochemical Society*, 1993.

Mills, A.; Lepre, A., "Controlling the Response Characteristics of Luminescent Porphyrin Plastic Film Sensors for Oxygen", *Anal. Chem.* 1997, 69, 4653–4659.

Lee, S.K.; Okura, I. "Photoluminescent Determination of Oxygen Using Metalloporphyrin–Polymer Sensing Systems", *Spectrochim. Acta* 1998, 54A, 91–100.

Amao, Y.; Asai, K.; Miyashita, T.; Okura, I., "Novel Optical Oxygen Pressure Sensing Materials: Platinum Porphyrin-Styrene–Trifluoroethylmethacrylate Copolymer Film", *Chem. Lett.* 1999, 1031–1032.

Prince, Barry J.; Schwabacher, Alan W.; Geissinger, Peter, "A Readout Scheme Providing High Spatial Resolution for Distributed Flourescent Sensors on Optical Fibers",*Anal. Chem.*, 2000, p. Est:8.4 (A–I).

Dakin, J.P., "Distributed Optical Fiber Sensors", *Proc. SPIE–Int. Soc. Opt. Eng.*, 1797, (1992), 76–108.

Potyrailo, R.A.; Hieftje, G.M., "Optical Time–of–Flight Chemical Detection: Spatially Resolved Analyte Mapping with Extended–Length Continuous Chemically Modified Optical Fibers",*Anal. Chem.*, 1998, 70, 1453–1461.

Potyrailo, R.A.; Hieftje, G.M., "Optical Time–of–Flight Chemical Detection: Absorption–Modulated Fluorescence for Spatially Resolved Analyte Mapping in a Bidirectional Distributed FiberOptic Sensor" *Anal. Chem.* 1998, 70, 3407–3412.

Potyrailo, R.A.; Hieftje, G.M., "Spatially Resolved Analyte Mapping with Time–of–Flight Optical Sensors", *Trends Anal. Chem.*, 1998, 17, 593–604.

Van Dover, R.B.; Schneemeyer, L.F.; Fleming, R.M., "Discovery of a Useful Thin–Film Dielectric Using a Composition–Spread Approach", *Nature*, vol. 392, 1998, pp. 162–164.

Hanak, J.J., "The 'Multiple–Sample Concept' in Materials Research: Synthesis, Compositional Analysis and Testing of Entire Multicomponent Systems", *Journal of Materials Science*, 1970, pp. 964–971.

Ward, Michael D.; Buttry, Daniel A., "In Situ Interfacial Mass Detection with Piezoelectric Transducers", *Science*, vol. 249, 1990, pp. 1000–1007.

Hierlemann, A., Ricco, A.J.; Bodenhöfer, K.; Göpel, W., "Effective Use of Molelcular Recognition in Gas Sensing: Results From Acoustic Wave and in Situ FT–IR Measurements", *Anal. Chem.*, 1999, 71, pp. 3022–3035.

Thomas, R.C.; Hierlemann, A.; Staton, A.W.; Hill, M.; Ricco, A.J., "Reflectance Infrared Spectroscopy on Operating Surface Acoustic Wave Chemical Sensors During Exposure to Gas–Phase Analytes", *Anal. Chem.*, 1999, 71, pp. 3615–3621.

Furuki, M; Lyong, S.P., "Hybrid Gas Detector of Squarylium Dye Langmuir–Blodgett Film Deposited on a Quartz Oscillator", *Thin Solid Films*, 1992, pp. 471–473.

Furiki, M.; Lyong, S.P., "Gas Detection by a Multi–Hybrid Sensor with Dye Langmuir–Blodgett Films Deposited on a Quartz Oscillator", *Mol. Cryst. Liq. Cryst.*, 1993, 227, pp. 325–337.

\* cited by examiner

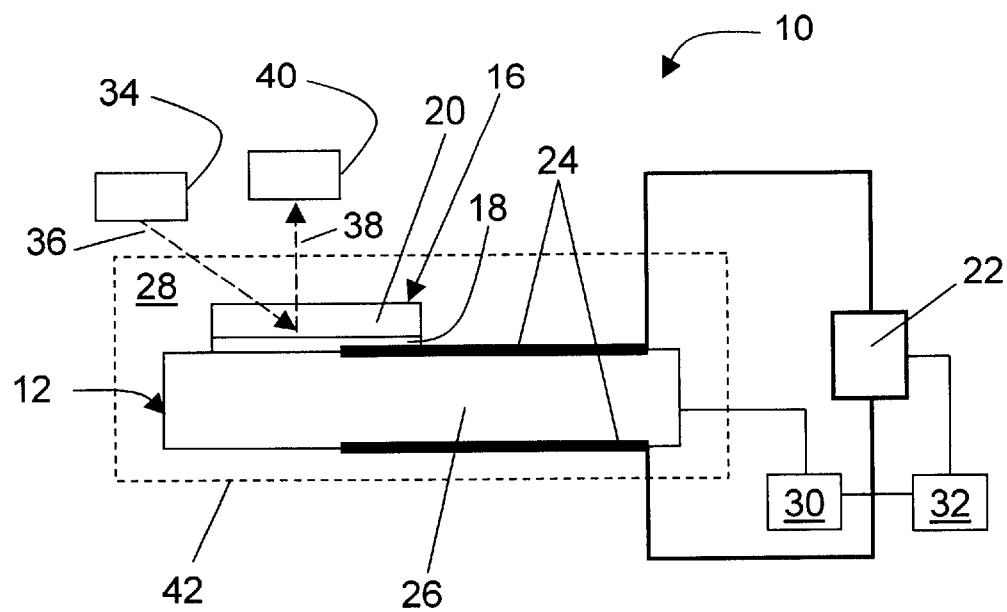

LEGEND: 10 – Luminescence/Scattering System, 12 – Dual Response Transducer, 16 – Coating Structure, 18 – Sensing Material, 20 – Barrier Coating, 22 – Power Source, 24 – Electrodes, 26 – Substrate, 28 – Fluids, 30 – Acoustic Measurement Device, 32 – Computer, 34 – Radiation Source, 36 – Reference Radiation, 38 – Resulting Radiation, 40 – Detector, 42 – Gas Cell

FIGURE 1

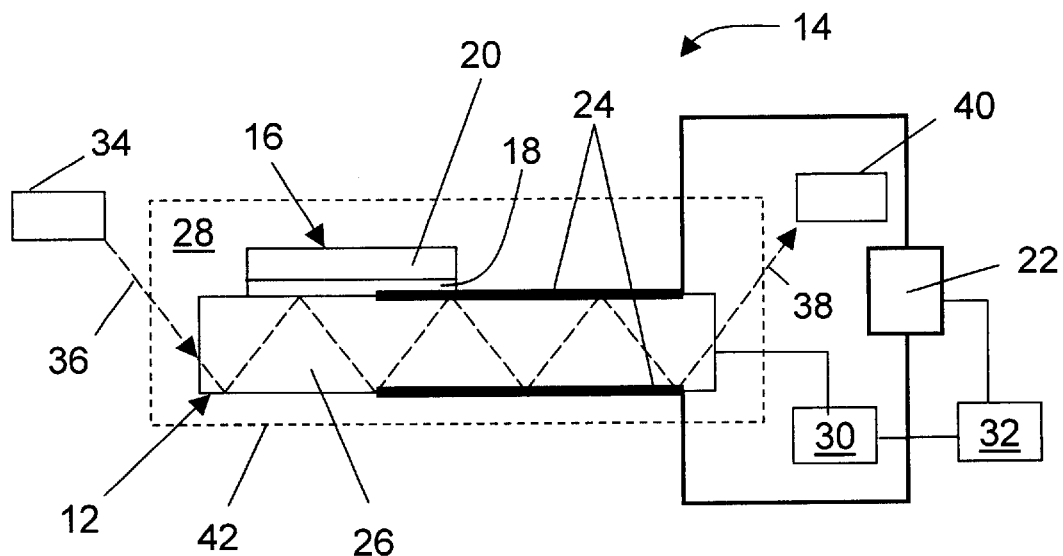

LEGEND: 12 – Transducer, 14 – Evanescent-Wave System, 16 – Coating Structure, 18-Sensing Material, 20 – Barrier Coating, 22 – Power Source, 24 – Electrodes, 26 – Substrate, 28 – Fluids, 30 – Acoustic Measurement Device, 32 – Computer, 34 – Radiation Source, 36 – Reference Radiation, 38 – Resulting Radiation, 40 – Detector, 42 – Gas Cell

FIGURE 2

LEGEND: 12 – Transducer, 13 – Planar Waveguide Transducer, 18 – Sensing Material, 20 – Barrier Coating, 28 – Fluids LEGEND: 84 – Transducer; 86 – Base, 88 – Array of Wells, 90-Individual Well LEGEND: 12 – Transducer, 18 – Sensing Material, 20 – Barrier Coating, 26 – Substrate, 28 – Fluid(s), 110 – Set-up, 112 – Sensor, 114 – Gas Impermeable Cell, 116 – Coating/Substrate Structure

US 6,567,753 B2

DEVICES AND METHODS FOR SIMULTANEOUS MEASUREMENT OF TRANSMISSION OF VAPORS THROUGH A PLURALITY OF SHEET MATERIALS

FEDERAL RESEARCH STATEMENT

The U.S. Government may have certain rights in this invention pursuant of NIST contract number 70NANB9H3038.

BACKGROUND OF INVENTION

This invention relates to real-time measurements of transport of different vapors into a plurality of barrier coatings, and specifically, these measurements are performed using a combination of acoustic wave and optical detection.

Barrier polymers, for example, are used for many packaging and protective applications. As barriers, these materials typically separate a system, such as an electronic component, a part of an engineering structure, or an article of food, from an environment. Often, such polymers are applied as coatings from liquid coating formulations. To adjust viscosity of the formulations, a wide variety of organic solvents are used.

In combinatorial discovery of coating materials for application as barrier coatings, rapid evaluation of permeability of coatings is of primary importance. Transport of vapors in coatings is typically measured by exposing one side of the coating to an analyte vapor, while nitrogen gas sweeps the other side of the coating to a detector. The detector measures the rate that the analyte vapor penetrates the coating. Another method employs the measurement of the amount of an outgassed vapor when a barrier coating is deposited onto a non-permeable substrate and is exposed to a vapor of interest.

Acoustic wave and optical sensors are useful, for example, for quantitation of chemical species by observing the changes in respective detected parameters as a function of analyte concentration. Often, these measurements produce a non-specific sensor response, making the identification of species problematic. To improve selectivity of sensor response, several methods are known, including pattern recognition of responses from several broadly responsive transducers. Other methods involve measurements of several parameters from a single sensor. Velocity and attenuation of an acoustic wave traveling through a sensing film has been measured in a single acoustic wave transducer. Optical measurements have been combined with acoustic wave measurements in chemical sensors. Surface acoustic wave sensor measurements have been combined with direct in situ Fourier transform infrared external-reflectance spectroscopy. Luminescence intensity and the oscillation frequency of a luminescent monomolecular laminated sensing film have been measured from a single acoustic wave transducer. However, these methods suffer from the impossibility of measurements of barrier properties of multiple coating materials toward several vapors of interest.

SUMMARY OF INVENTION

Thus, there remains an unmet need to provide devices and methods that avoid the need to use a large coating area to obtain measurable signals. There also remains a need to address difficulties in evaluation of multiple coatings simultaneously, and to address difficulties in measuring the permeability of coatings with respect to several fluids, for example, at once.

In one embodiment, a system for determining barrier properties of a barrier coating, comprises: at least one sensor having at least one external surface, the at least one sensor responsive to interactions with a plurality of fluids; at least one barrier coating associated with each sensor, each sensor having initial characteristics and subsequent characteristics each associated with the barrier properties of the coating with respect to each of a plurality of fluids, where the initial characteristics correspond to the barrier coating properties prior to exposure to any of the plurality of fluids and the subsequent characteristics correspond to the barrier coating properties after exposure to at least two of a plurality of fluids, the initial characteristics for each barrier coating associated with an initial optical property and an initial acoustic wave property, and the subsequent characteristics of each barrier coating associated with a subsequent optical property and a subsequent acoustic wave property; an optical characteristic measurement device for measuring the initial optical property and subsequent optical property associated with each barrier coating; an acoustic wave property measurement device for measuring the initial acoustic wave property and the subsequent acoustic wave property associated with each barrier coating; and a computer for determining a first barrier property and a second barrier property of each barrier coating, the first barrier property with respect to one of the two of the plurality of fluids, the second barrier property with respect to the other of the two of the plurality of fluids, the first barrier property and the second barrier property based on the variation between the initial characteristics and subsequent characteristics associated with both the optical properties and the acoustic wave property of each barrier coating.

In another embodiment, a system for determining barrier properties of a barrier coating, comprises: a plurality of sensors each having at least one external surface; a plurality of barrier coatings, each of the plurality of barrier coatings associated with a corresponding one of the plurality of sensors, each sensor having initial characteristics and subsequent characteristics each associated with the barrier properties of the barrier coating with respect to each of a plurality of fluids, where the initial characteristics correspond to the barrier coating properties prior to exposure to any of the plurality of fluids and the subsequent characteristics correspond to the barrier coating properties after exposure to at least two of a plurality of fluids, the initial characteristics for each sensor associated with an initial optical property and an initial acoustic wave property, and the subsequent characteristics of each sensor associated with a subsequent optical property and a subsequent acoustic wave property; an optical characteristic measurement device for measuring the initial optical property and the subsequent optical property associated with each of the plurality of barrier coatings; a acoustic wave property measurement device for measuring the initial acoustic wave property and subsequent acoustic wave property associated with each of the plurality of barrier coatings; a processing device for determining a first barrier property and a second barrier property of each of the plurality of barrier coatings, the first barrier property with respect to one of the two of the plurality of fluids, the second barrier property with respect to the other of the two of the plurality of fluids, the first barrier property and the second barrier property based on the variation between the initial characteristics and subsequent characteristics associated with both the optical properties and the acoustic wave property of each barrier coating; and wherein the subsequent optical property and the corresponding subsequent acoustic wave property associated with each barrier coating are simultaneous measurements.

In still another embodiment, a method for screening for barrier properties of a barrier coating, comprises: measuring initial characteristics associated with at least one barrier coating associated with at least one corresponding sensor responsive to a plurality of fluid, the initial characteristics including an initial acoustic wave property and an initial optical property; exposing each barrier coating to at least two of the plurality of fluids; measuring subsequent characteristics associated with the least one barrier coating, the subsequent characteristics including a subsequent acoustic wave property and a subsequent optical property; determining a first barrier property and a second barrier property associated with the at least one barrier coating with respect to the at least two of the plurality of fluids based on the initial characteristics and subsequent characteristics.

In yet another embodiment, a method for screening for barrier properties of a barrier coating, comprises: measuring initial characteristics associated with at least one barrier coating associated with at least one corresponding sensor responsive to a plurality of fluids, the initial characteristics including an initial acoustic wave property and an initial optical property; exposing each barrier coating to at least two of the plurality of fluids; simultaneously measuring subsequent characteristics associated with the least one barrier coating, the subsequent characteristics including a subsequent acoustic wave property and a subsequent optical property; determining a first barrier property and a second barrier property associated with the at least one barrier coating with respect to the at least two of the plurality of fluids based on the initial characteristics and subsequent characteristics, where the initial characteristics are measured prior to the exposure to the fluids and the subsequent characteristics are measured subsequent to exposure to the fluids.

In another embodiment, a system for determining barrier properties of a barrier coating, comprises: at least one sensor having at least one external surface, the at least one sensor responsive to interactions with a plurality of fluids; a gas-impermeable cell having an interior chamber, the at least one sensor positioned within the interior chamber; at least one barrier coating associated with each sensor, each sensor having initial characteristics and subsequent characteristics each associated with the barrier properties of the coating with respect to each of a plurality of fluids, where the initial characteristics correspond to the barrier coating properties prior to exposure to any of the plurality of fluids and the subsequent characteristics correspond to the barrier coating properties after exposure to at least two of a plurality of fluids, the initial characteristics for each barrier coating associated with an initial optical property and an initial acoustic wave property, and the subsequent characteristics of each barrier coating associated with a subsequent optical property and a subsequent acoustic wave property; a substrate attachable to the gas-impermeable cell so as to seal the interior chamber, wherein the at least one barrier coating is associated with the substrate; an optical characteristic measurement device for measuring the initial optical property and subsequent optical property associated with each barrier coating; an acoustic wave property measurement device for measuring the initial acoustic wave property and the subsequent acoustic wave property associated with each barrier coating; and a computer for determining a first barrier property and a second barrier property of each barrier coating, the first barrier property with respect to one of the two of the plurality of fluids, the second barrier property with respect to the other of the two of the plurality of fluids, the first barrier property and the second barrier property based on the variation between the initial characteristics and subsequent characteristics associated with both the optical properties and the acoustic wave property of each barrier coating.

BRIEF DESCRIPTION OF DRAWINGS

FIG. 1 is a dual-response transducer for acoustic wave and optical measurements in the luminescence or scattering mode in accordance with an embodiment of the present invention;

FIG. 2 shows a dual-response transducer for acoustic wave and optical measurements in the evanescent-wave mode, with the evanescent-wave interactions of the propagated light with the deposited coating material detected in accordance with an embodiment of the present invention;

DETAILED DESCRIPTION

Figure 3:
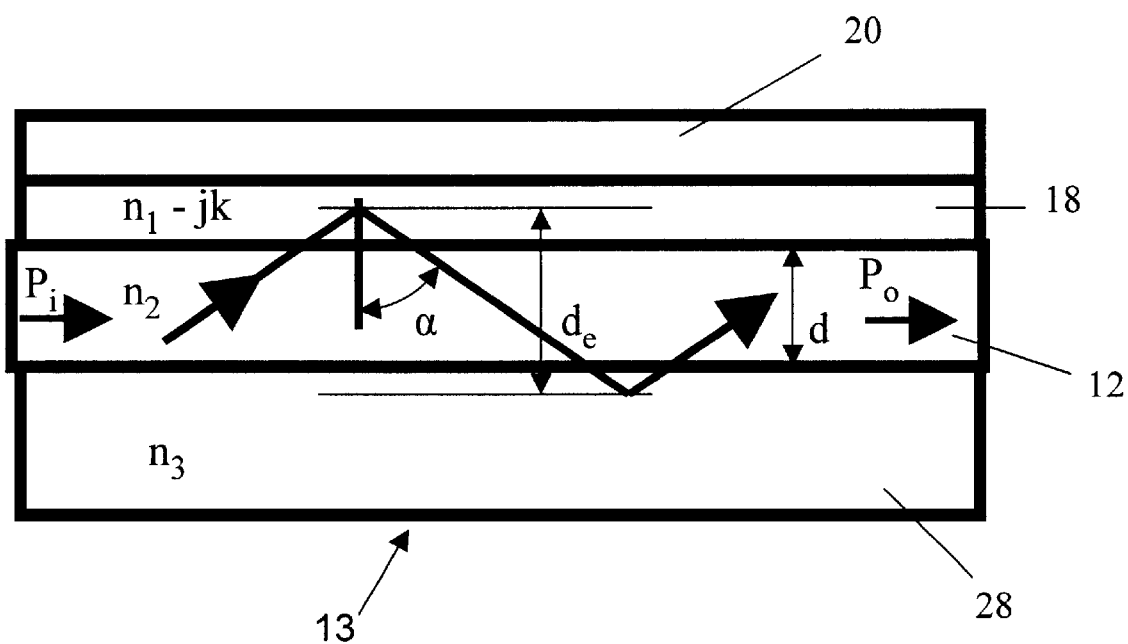
FIG. 3 is a schematic diagram of one embodiment of a device for producing simultaneous evaluation of oxygen and moisture transport properties in multiple barrier coatings.

In accordance with embodiments of the present invention, the transmission rate characteristics, or barrier properties, of each individual coating within an array of barrier coatings are simultaneously measurable with respect to each of a plurality of fluids exposed to the array. These measurements are performed using an array of dual-response transducers. Each of these transducers simultaneously measures the optical property and the acoustic wave property of a coating structure, including a barrier coating deposited onto a sensing layer. The optical property may be correlated with a first barrier property of an individual coating with respect to one of the plurality of fluids, while the acoustic wave property of the individual coating may be correlated with a second barrier property of the coating with respect to a different one of the plurality of coatings.

Several configurations of acoustic wave transducers can be useful. These configurations can be described based on their unique acoustic modes, such as thickness-shear mode (TSM), surface acoustic wave (SAW), acoustic plate mode (APM), flexural plate wave (FPW), and surface transverse wave (STW) devices. For further details, refer to Ballantine, D. S., Jr.; White, R. M.; Martin, S. J.; Ricco, A. J.; Frye, G. C.; Zellers, E. T.; Wohltjen, H. *Acoustic Wave Sensors: Theory, Design, and Physico-Chemical Applications*, chapters 3 and 6, Academic Press: San Diego, Calif., 1997.

The sensing layer is doped with a reagent sensitive to one or more of the fluids, for example gases, solvents or other fluids such as molecular oxygen and moisture. The change in the acoustic wave property of the transducer is associated with the changing material parameters of the oscillating crystal due to the permeation of one or more fluids into the coating structure. These material parameters include the change in property of the deposited material such as density, viscosity, mass, and crystallinity. These properties can be measured separately by monitoring a variety of parameters from a one- or two-port acoustic-wave device. These measured parameters include: fundamental oscillation frequency, harmonic oscillation frequency, impedance phase and magnitude of one-port devices, impedance phase and attenuation of two-port devices, wave velocity and wave attenuation, capacitance, and conductance.

Permeation of the fluids through the barrier coating and into the sensing layer also results in a change in one or more optical properties of the sensing layer. This optical property can be absorbance (e.g., ultraviolet (UV), visible, infrared), luminescence, Raman scattering, refractive index, or a combination of these properties. The variation in acoustic wave property and the variation in optical properties are measured and utilized to determine a relative performance of each barrier coating in the array with respect to barrier properties corresponding to each of the plurality of fluids. Further, the measured variations may be correlated with a standard transmission rate or barrier property characteristic for each coating in the array.

FIGS. 1 and 2 present embodiments of two configurations for the measurement of the transmission rate of one or more fluids through a coating structure to determine its barrier properties. Although only a single coating structure and transducer are shown, it is understood that these configurations may be utilized in an array format to simultaneously screen a plurality of coating structures. In each configuration, a dual-response transducer for acoustic wave and optical measurements permits monitoring of the transport of several gases into the barrier coatings simultaneously. FIG. 1 presents a luminescence or scattering mode set-up 10 utilizing a dual-response transducer 12 for acoustic wave and optical measurements. FIG. 2 presents an evanescent-wave mode set-up 14, utilizing the dual-response transducer 12 for acoustic wave and optical measurements.

In FIGS. 1 and 2, a coating structure 16 is deposited onto the dual-response transducer 12. The coating structure 16 includes a sensing material 18 and a barrier coating 20. The sensing material 18 may be deposited as a separate layer onto the transducer 12, or the sensing material may be incorporated into the composition of the barrier coating 20. A single substrate 26 serves as both an acoustic wave device and an optical transducer. The coating structure 16 may be deposited on a single or several surfaces of the substrate 26. The coating structure 16 may have the sensing materials 18 tailored individually for individual components of a plurality of fluids 28 where individual sensing materials are probed by acoustic wave and/or optical methods. In an acoustic wave mode, an oscillation source such as a power source 22 provides an electrical potential to a pair of electrodes 24 positioned on opposite sides of a substrate 26, where the electrodes and substrate define the transducer 12, and where the electrical potential induces the transducer to oscillate at a given frequency.

Measurement of the acoustic-wave property of the baffler coating 20 and/or sensing material 18, associated with penetration of the coating structure 16 by at least one of a plurality of fluids 28 is made using a measurement device or devices 30 that measures a change in the acoustic wave property of the transducer 12. Examples of measurement device 30 for measuring acoustic-wave properties include electronic equipment such as a network analyzer, a vector voltmeter, an impedance analyzer, frequency counter, a phase interferometer, and an in-phase and quadrature demodulator. These measured parameters include: fundamental oscillation frequency, harmonic oscillation frequency, impedance phase and magnitude of one-port devices, impedance phase and attenuation of two-port devices, wave velocity and wave attenuation, capacitance, and conductance.

A computer 32 associated with the acoustic wave property measurement device 30 includes software for analyzing the change in acoustic wave property and correlating the change in acoustic wave property to a change in material parameter or parameters, and also into a predetermined barrier property metric. In an optical mode, a light source 34 delivers reference radiation 36 toward the transducer 12 and coating structure 16. Resulting radiation 38 is received by a detector 40, such as a photodetector, which measures any impacts or variations between the reference radiation 36 and the resulting radiation 38 that may be associated with penetration of the coating structure 16 by at least one of the plurality of fluids 28. The computer 32 further includes software for analyzing the detected and measured resulting radiation 38 and correlating the impacts on the light to a predetermined barrier property metric. In both configurations 10 and 14, the plurality of fluids 28 and the coating structure 16 are contained with a gas cell 42, which at least encompasses the coating structure. Therefore, in each configuration 10 and 14, a transducer 12 is utilized to simultaneously measure changes in the optical properties and acoustic wave properties of the coating structure 16, where the measured optical and mass changes are simultaneously correlated to a predetermined barrier property metric with respect to different ones of the plurality of fluids 28.

Among other features, this invention discloses the use of acoustic wave and optical transducers for evaluation of barrier properties of coatings. These measurements are performable in a number of formats, including the following:

1) as applied to barrier coatings deposited onto a transducer device and exposed to a fluid of interest;
2) as applied to barrier coatings deposited onto a sensing material deposited onto a transducer device and exposed to a fluid of interest; and
3) as applied to barrier coatings where one side of the barrier coating is exposed to a fluid and the other side of the barrier coating is in proximity to a stand-alone sensing material or a combination of sensing materials deposited onto a transducer.

In all of the above cases, the measurement principle is based on the rapid determination of minute changes in properties of material deposited onto the surface of a dual mode (acoustic wave and optical) transducer. Several configurations of acoustic wave transducers are applicable. These configurations can be described based on their unique acoustic modes, such as thickness-shear mode (TSM), surface acoustic wave (SAW), acoustic plate mode (APM), flexural plate wave (FPW), and surface transverse wave (STW) devices. For further details, refer to Ballantine, D. S., Jr.; White, R. M.; Martin, S. J.; Ricco, A. J.; Frye, G. C.; Zellers, E. T.; Wohltjen, H. *Acoustic Wave Sensors: Theory, Design, and Physico-Chemical Applications*; chapters 3 and 6, Academic Press: San Diego, Calif., 1997.

Other types of piezoelectric devices are easily adaptable for the various applications described for this invention, as will be understood by those familiar with the art. These devices are typically of about ⅛ inch to about 2 inches in diameter and 10 microns to 2 mm in thickness, although other shaped and sized devices may be utilized. Further, for example, the minute quantity of coating material may be in the range of about 1 picogram to about 1 milligram, more preferably about 100 picogram to about 10 milligram, and most preferably about 1 nanogram to about 1 microgram. The quantity of the material will depend upon the operating frequency of the device.

For example, in a thickness-shear mode (TSM) device, an oscillating potential is applied to electrodes deposited onto two opposite sides of a piezoelectric material, such as a quartz crystal. This piezoelectric material oscillates in the thickness-shear mode with a fundamental frequency measured using a conventional frequency counter. Such a piezoelectric TSM transducer allows measurement of such variations as the change in mass of, or applied to, the oscillating crystal, after accounting for other factors such as the dimensions and other parameters of the crystal, as well as variables, such as the temperature at which measurement is made. When a sensing material or barrier coating material is deposited onto a transducer device and is exposed to a fluid, the material may experience a change in a material parameter or parameters such as density, viscosity, mass, and crystallinity, depending on the barrier properties of the coating with respect to the fluid.

The sensing material and the barrier coating may be applied to the transducer using thin-film deposition techniques in combination with physical masking techniques or photolithographic techniques. Such thin-film deposition techniques can generally be broken down into the following four categories: evaporative methods, glow discharge processes, gas-phase chemical processes, and liquid-phase chemical techniques. Included within these categories are, for example, sputtering techniques, spraying techniques, laser ablation techniques, electron beam or thermal evaporation techniques, ion implantation or doping techniques, chemical vapor deposition techniques, as well as other techniques used in the fabrication of integrated circuits. All of these techniques can be applied to deposit highly uniform layers, i.e., thin-films, of the various coatings on selected regions on the transducer. For an overview of the various thin-film deposition techniques which can be used in the methods of the present invention, see, for example, *Handbook of Thin-Film Deposition Processes and Techniques*, Noyes Publication (1988), which is incorporated herein by reference. Other types of coating procedures are also easily applicable in conjunction with the methods of the present invention to deposit the barrier coatings. These other coating procedures include, for example, spin-coating, brushing, and laser deposition. See for example, Ballantine, D. S., Jr.; White, R. M.; Martin, S. J.; Ricco, A. J.; Frye, G. C.; Zellers, E. T.; Wohltjen, H. *Acoustic Wave Sensors: Theory, Design, and Physico-Chemical Applications*; Chapter 6, Academic Press: San Diego, Calif., 1997.

The mass change of the oscillating crystal of a TSM device is determined from the change in the resonant frequency of the crystal according to the Sauerbrey equation, as follows:

$$\Delta f = -2 f_0^2 (m/A)(\mu_Q \rho_Q)^{-\frac{1}{2}} \quad (1)$$

where $\Delta f$ is the change in resonant frequency upon material deposition or removal, $f_0$ is the fundamental resonant frequency of the unloaded device, $\mu_Q$ is the shear modulus of the piezoelectric substrate, $\rho_Q$ is the substrate density, m is the total mass of the material deposited on the crystal, and A is the active surface area of one face of the crystal.

In one example embodiment, piezoelectric transducers used in conjunction with the methods and devices of this invention are 10-MHz AT-cut quartz crystals with an active electrode area of 0.2 cm². The mass sensitivity of a crystal per unit of frequency change is:

$$m/\Delta f = -A/(2 f_0^2)(\mu_Q \rho_Q)^{-\frac{1}{2}} \quad (2)$$

The minus sign indicates that, upon increase in mass, the oscillation frequency decreases, while upon decrease in mass, the oscillation frequency increases. For the AT-cut quartz of this embodiment, $\mu_Q = 2.947 \times 10^{11}$ g·cm⁻¹·s⁻² and $\rho_Q = 2.648$ g·cm⁻³. Thus, the mass sensitivity of the device for this embodiment is as follows:

$$m/\Delta f = 0.883 \times 10^{-9} \text{ g·Hz}^{-1} \quad (3)$$

The above relationship demonstrates that the piezoelectric device of this embodiment is able to detect the mass change of 0.883 nanograms when the resolution of the frequency measurement is 1 Hz, which is a typical noise level of frequency measurements. The mass sensitivity is easily improvable when an adequate gate time and temperature stabilization are utilized for frequency measurements. For example, in this case, the noise in frequency measurement is reducible to 0.05 Hz, which provides a mass resolution of 44 picograms. The mass resolution of such measurements is thus approximately six orders of magnitude higher than conventional laboratory scale balances.

From equation (1) above, the change in resonant frequency $\Delta f_F$ upon deposition of a film is relatable to the thickness of the film deposited onto the crystal, as follows:

$$\Delta f_F = -4f_0^2 \rho_F d_F (\mu_q \mu_Q \rho_Q)^{-1/2} \quad (4)$$

where $\rho_F$ and $d_F$ are, respectively, the density and thickness of the film. For the AT-cut quartz crystal oscillating at 10 MHz in accordance with the embodiment above; the film thickness (in cm) is given by the following equation:

$$d_F = 2.2 \times 10^{-9} \Delta f_F / \rho F \quad (5)$$

A barrier property of the film may be expressed in relation to the frequency change during and/or after exposure to the fluid. Correlation between a barrier property and the signal collected with the TSM acoustic wave transducer is performed for all formats of operation.

In one measurement format, a barrier coating is deposited onto a transducer device and exposed to at least one of a plurality of fluids. The frequency measurements are performed on the transducer device:

1. before deposition of the coating onto the crystal,
2. after deposition of the coating onto the crystal but before exposure to the fluid to establish the amount of deposited coating, and
3. during the exposure to the fluid to establish the amount of fluid absorbed into the coating at each given period of time.

In another measurement format, a barrier coating is deposited onto a sensing material which is deposited onto a transducer device and exposed to at least one of a plurality of fluids. The frequency measurements are performed on the transducer device:

1. before deposition of the coating onto the sensing material,
2. after deposition of the coating onto the sensing material but before exposure to the fluid to establish the amount of deposited coating, and
3. during the exposure to the fluid to establish the amount of fluid absorbed into the coating and into the sensing material at each given period of time.

In yet another measurement format, a barrier coating is attached to an opening of a fluid cell and one side of the barrier coating is exposed to at least one of a plurality of fluids and the other side of the barrier coating is in proximity to a sensing material or a combination of sensing materials deposited onto a transducer. The frequency measurements are performed on the transducer device:

1. before exposure of the barrier coating to the fluid to establish the baseline response of the transducer and
2. during the exposure of the barrier coating to the fluid to establish the amount of fluid transported to the other side of the coating and absorbed into the sensing material at each given period of time.

Thus, the above equations for TSM transducers, and other equivalent equations for other types of acoustic wave transducers having other given parameters, may be utilized to determine a change in acoustic wave properties of a given transducer, which is a function of the fluid transport properties of the barrier coating deposited on the transducer or located in proximity to the transducer. Therefore, as the change in acoustic wave property is associated with a penetration of the barrier coating by at least one of the plurality of fluids, the measured change in acoustic wave property corresponds to a barrier property metric for the given coating with respect to the at least one fluid.

Similarly, the change in optical properties of radiation or light interacting with the barrier coating and/or the sensing material may be attributed to penetration of the barrier coating by at least one of the plurality of fluids. The change in optical properties of the radiation or light caused by a fluid partitioned or interacted into the sensing layer, is detectable as a change in such properties as absorbance, scattering, refractive index, or luminescence. The impact on the radiation or light is defined as a measurable change in the radiation or light, such as a variation in intensity, frequency, polarization state, phase and temporal properties of the wave. The reference radiation 36 has a predetermined range of one or more characteristics, including intensity, wavelength, polarization state, phase and temporal properties. For example, the predetermined range for intensity may be in the range of about a single photon to about 1 kilowatt, or from about a single photon to about 0.1 kilowatt. For wavelength, from about 10 nanometers–50 micrometers, or from about 150 nanometers 20 micrometers. For polarization state, from about 0 to 360 degrees. For phase difference, from about 0.001 to 10000 wavelengths of probe radiation, preferably from about 0.01 to 1000 wavelengths of probe radiation, and most preferably from about 0.1 to 100 wavelengths of probe radiation. For a temporal property such as luminescence lifetime, from about 10 picoseconds–1000 seconds, preferably about 100 picosecond–1 second, and more preferably about 1 nanosecond 100 milliseconds. For a temporal property such as time delay, from about 1 femtosecond–1000 seconds, preferably about 100 femtoseconds–1 second, and more preferably from about 1 picosecond 100 milliseconds.

For example, the reference radiation 36 may be a pulsed wave or a continuous wave of radiation. Similarly, the resulting radiation 38 has a predetermined range of one or more characteristics, including amplitude, frequency, wavelength, polarization state, phase and temporal properties, similar to the ranges mentioned above. For both the reference radiation 36 and the resulting radiation 38, the predetermined range of characteristics may vary depending on the barrier coating 20, sensing layer 18, fluids 28 and detection/measuring capabilities being utilized. Further, for the resulting radiation 38, the measured value of one or more of the characteristics may be utilized to determine the relative barrier property of the coating with respect to a given fluid.

For example, in detecting luminescence, the reference radiation 36 has a predetermined range of characteristics that excite the sensing layer 18 if exposed to any given one of the fluids 28, thereby promoting luminescence and providing the resulting radiation 38. The resulting radiation 38 is typically of a substantially different intensity relative to excitation light, when exposed to one or more fluids 28, than the reference radiation 36 and the value of, for example, its intensity may be correlated to a barrier property of the coating with respect to any given one of the fluids 28.

Similarly, the resulting radiation 38 is typically of a substantially different wavelength relative to excitation light, when exposed to one or more fluids 28, than the reference radiation 36 and the value of, for example, its wavelength may be correlated to a barrier property of the coating with respect to any given one of the fluids 28.

Similarly, the resulting radiation 38 is typically of a substantially different polarization relative to excitation light, when exposed to one or more fluids 28, than the reference radiation 36 and the value of, for example, its polarization may be correlated to a barrier property of the coating with respect to any given one of the fluids 28.

Similarly, the resulting radiation 38 is typically of a substantially different phase relative to excitation light, when exposed to one or more fluids 28, than the reference radiation 36 and the value of, for example, its phase may be correlated to a barrier property of the coating with respect to any given one of the fluids 28.

Similarly, the resulting radiation 38 is typically of a substantially different temporal property such as luminescence lifetime relative to excitation light, when exposed to one or more fluids 28, than the reference radiation 36 and the value of, for example, its temporal property such as luminescence lifetime may be correlated to a barrier property of the coating with respect to any given one of the fluids 28.

For both the reference radiation 36 and the resulting radiation 38, the predetermined range of characteristics may vary depending on the barrier coating 20, sensing layer 18, fluids 28 and detection/measuring capabilities being utilized. Further, for the resulting radiation 38, the measured value of one or more of the characteristics may be utilized to determine the relative barrier property of the coating with respect to a given fluid.

For example, in detecting luminescence, the reference radiation 36 has a predetermined range of characteristics that excite the sensing layer 18 if the sensing layer is exposed to any given one of the fluids 28, thereby promoting luminescence and providing the resulting radiation 38. Compared to the reference radiation 36, the resulting radiation 38 is typically of a substantially different, known wavelength when the sensing layer is exposed to one or more fluids 28. The value of, for example, the intensity or luminescence lifetime change of the resulting radiation 38 may be correlated to a barrier property of the coating with respect to a given one of the fluids 28.

For example, in detecting scatter, the reference radiation 36 has a predetermined range of characteristics that may vary if the barrier coating 20 is penetrated by any given one of the fluids 28. Therefore, the resulting radiation 38 has a different set of characteristics that vary from the reference radiation 36, where the difference between the values of the characteristics may be correlated to a barrier property of the coating with respect to any given one of the fluids 28.

For example, in the transmission mode, the reference radiation 36 is propagated through the substrate 26 and is impacted by interacting with the sensing layer 18 to produce the resulting radiation 38. The resulting radiation 38 may have an initial set of characteristics that vary from the characteristics of the reference radiation 36 due to the properties of a given sensing layer 18, prior to the penetration of any fluid 28. Further, the resulting radiation 38 may have an adjusted set of characteristics due to interaction with the sensing layer 18 after the sensing layer has been penetrated by any given one of the fluids 28. These adjusted characteristics may include variations in the characteristics of the reference radiation or they may include characteristics of a new radiation caused by, for example, luminescence of the sensing layer. The difference between the initial and adjusted characteristics of the resulting radiation 38 may be utilized to determine relative barrier properties of the barrier coating with respect to a given one of the fluids 28.

In case of an absorbing sensing layer, absorbance A of the sensor layer may be described as:

$$A = \epsilon C_C L C_F \quad (6)$$

where $\epsilon$ is the molar extinction coefficient of the sensor material, L is thickness of the sensing layer, $C_C$ is a reagent concentration in the coating, and $C_F$ is the concentration of the fluid sorbed into the sensing film. As the concentration of the fluid increases due to the permeation of the fluid through a barrier coating into the sensing material, absorbance A of the sensing layer increases and is detected by an optical system.

In case of a luminescent sensing layer, intensity of the light l emitted from the sensing layer may be represented as $$l = I_0 \Phi \epsilon C_C L C_F \quad (7)$$

where $I_0$ is intensity of excitation light, $\Phi$ is quantum yield of a given chemically sensitive luminophore, $\epsilon$ is molar extinction coefficient at the excitation wavelength of a given reagent, $C_C$ is the reagent concentration in the coating, L is thickness of the sensing layer, and $C_F$ is the concentration of the fluid sorbed into the sensing film. As the concentration of the fluid increases due to the permeation of the fluid through a barrier coating into the sensing material, luminescence l of the sensing layer increases and is detected by an optical system.

In another chemical design of the luminescent sensing layer, intensity of the light l emitted from the sensing layer can be dynamically quenched in presence of a fluid and may be related to the intensity of light $l_0$ emitted from the sensing layer in the absence of the fluid as described by the Stern-Volmer equation given by $$I_0/I = 1 + K_{SV} C_F \quad (8)$$

where $K_{SV}$ is the Stern-Volmer quenching constant. As the concentration of the fluid increases due to the permeation of the fluid through a barrier coating into the sensing material, luminescence I of the sensing layer decreases and is detected by an optical system. Similarly, other luminescence parameters may be detected, such as luminescence lifetime and polarization.

Optical absorption sensor may be in the form of a total-internal reflection transducer, such as a planar or cylindrical waveguide, a polygonal total-internal reflection ring resonator or other type of a total-internal reflection element. Such a total-internal reflection transducer can have a chemically sensitive film on one or more sides as depicted in FIG. 2. Performance of a total-internal reflection transducer may be described using a ray optics approach. Launching methods of light into a waveguide or other types of total-internal reflection transducer are well known. See, for example, Potyrailo, R. A.; Hobbs, S. E.; Hieftje, G. M., Optical waveguide sensors in analytical chemistry: today's instrumentation, applications and future development trends, Fresenius" J. Anal. Chem. 1998, 362, 349–373. A planar waveguide transducer 13 is schematically depicted in FIG. 3. The waveguide has a refractive index $n_2$. An absorbing chemical sensitive film that has a complex refractive index $n_c = n_1 jk$ is deposited onto one side of the transducer. The complex refractive index $n_c$ has a real part, $n_1$, which is refractive index and an imaginary part, k, which is an extinction coefficient, which is represented as $$k = 0.183 \epsilon C_F \lambda \quad (9)$$

where $\lambda$ is the wavelength of probe radiation. Another side of the transducer is exposed to a non absorbing medium with a refractive index $n_3$.

A guided mode in such transducer may be represented by the ray trajectory with the angle $\alpha$ between the light ray and the normal to the interface being determined by the standing wave conditions across the waveguide as described for example in G. Stewart and B. Culshaw, Optical waveguide modeling and design for evanescent field chemical sensors, *Optical and Quantum Electronics*, 26, S249–S259 (994). If the ray trajectory makes $\eta$ reflections per unit length in contact with the chemical species, then the attenuation of the guided wave due to the absorption in the chemically sensitive film is $$P_O/P_i=(|r|^2)\eta \quad (10)$$

where $P_O$ and $P_i$ are output and input optical powers and r is the reflection coefficient.

For the asymmetric planar waveguide shown in FIG. 3, with the chemically sensitive film on one side, number of reflections $\eta$ per unit length is given by $$\eta=(2n_e d_e)^{-1}(n_2^2-n_e^2)^{1/2} \quad (11)$$

where $n_e$ is the normalized propagation constant of the mode given by $n_e=n_2\sin\alpha$ and $d_e$ is the effective thickness of the mode, $d_e=d+1/Y_1+1/Y_3$ are decay constants of the evanescent fields in media 1 and 3 respectively. As the concentration of the fluid increases due to the permeation of the fluid through a barrier coating into the sensing material, absorbance of the sensing layer decreases causing the attenuation of the transmitted optical power through the waveguide.

If the optical luminescence sensor is in the form of a planar waveguide transducer with a chemically sensitive film on one or both sides of the waveguide as depicted in FIG. 2, its performance may be described using a ray optics approach. Each ray launched into the waveguide is considered an independent producer of luminescence. The net signal is obtained by adding the signals generated by each ray as described in Love, W. F.; Button, L. J.; Slovacek, R. E. Optical characteristics of fiber optic evanescent wave sensors, In Biosensors with Fiber optics; D. L. Wise and L. B. Wingard, Jr., Ed.; Humana Press: Clifton, N.J., 1991; pp 139–180. A thin film luminescent layer at the surface of the transducer may be treated by simply integrating over the layer:

$$I(\alpha) = \gamma I_{ray}(\alpha) \int_0^l F_{abs}(\delta;\alpha) P_{em}(\delta\theta_0^{max}) d\delta \quad (12)$$

where $\alpha$ is the angle between light ray and normal to interface; $\delta$ is distance of dipole from interface; $I(\alpha)$ is luminescence signal per unit area of transducer-sensing film interface; $\gamma$ is evanescent wave absorption coefficient; $1_{ray}(\alpha)$ is ray incident power normal to the interface for a given ray; $l$ is the thickness of the sensing film; $F_{abs}(\delta;\alpha)$ is normalized absorption function at distance $\delta$ into the evanescent region of the sensing material for light rays incident at angle $\alpha$; $P_{em}(\delta\theta_0^{max})$ is the probability of emisson into bound rays in the waveguide; and $\theta_0^{max}$ is the maximum angle with respect to the waveguide axis for the cone of external light rays that are launched into of collected from the waveguide, cone is defined by the experimental system. As the concentration of the fluid increases due to the permeation of the fluid through a barrier coating into the sensing material, luminescence of the sensing layer changes according to Equations 7 and 8 and is detected by an optical system.

Thus, by combining the acoustic wave and optical measurements performed on a single transducer, the barrier property of the deposited coating material may be determined relative to a different fluid associated with each measurement. For example, the acoustic wave measurement may be utilized to determine moisture permeability while the simultaneous optical measurement may be utilized to determine oxygen permeability.

The sensing layer 18 may be any material that does not change the properties of the deposited barrier coating 20 and that interacts with the plurality of fluids 28 in a manner that may be measured. Particularly, the interaction with the plurality of fluids may alter the characteristics of received radiation, or may produce luminescent radiation, or combinations of both. The composition of the sensing layer varies depending on the particular barrier property and barrier coating being analyzed. Characteristics of the sensing layer, such as absorption spectrum, refractive index, luminescence intensity, luminescence lifetime, luminescence spectrum, etc. may change upon exposure to any one of the fluids. To enhance the ability to detect the changes or impacts on the radiation, a chemically sensitive dye may be incorporated into the sensing layer or barrier coating film, or a dye molecule may be directly attached to a polymer molecule. In this manner, changes of optical properties of the dye are relatable to the variation of the chemical environment of the barrier coating. Therefore, as the change in optical properties are associated with a penetration of the barrier coating by at least one of the plurality of fluids, the measured change or impact on the light corresponds to a barrier property metric for the given coating with respect to the at least one fluid.

Luminophores are incorporated into the sensing layer, which may be formed from film-forming polymeric material. The material for the sensing layer may affect the properties of sensors such as selectivity, sensitivity, and limit of detection. Thus, suitable material for the sensing layer is selected from polymeric material capable of providing required response time, coating permeability, coating solubility, degree of transparency and hardness, and other similar characteristics relevant to the coating and the desired barrier property to be analyzed. Typical requirements for a sensing layer are described in Wolfbeis, O. S. In Fiber Optic Chemical Sensors and Biosensors; O. S. Wolfbeis, Ed.; CRC Press: Boca Raton, Fla., 1991; Vol. 2; pp 19–53 and Ballantine, D. S., Jr.; White, R. M.; Martin, S. J.; Ricco, A. J.; Frye, G. C.; Zellers, E. T.; Wohltjen, H.; Acoustic Wave Sensors: Theory, Design, and Physico-Chemical Applications; Academic Press: San Diego, Calif., 1997, p347 –355.

For example, in general polymers that can be used as matrices for oxygen sensors, for example, can be divided into several classes as described by: S. A. Stern, B. Krishnakumar, S. M. Nadakatti, Physical Properties of Polymers Handbook; J. E. Mark, Ed.; AIP Press: New York, 1996; pp 687–700. Such classes include polyolefins, vinyl and vinylidene polymers, natural and synthetic rubbers, polyesters, polycarbonates, cellulose derivatives, fluoropolymers, polyorganosiloxanes, polynitriles, polyamides, polyimides, polyurethanes, polyoxides, polysulfones, polyacetylenes, polyacrylics. A variety of polymeric materials useful for incorporation of oxygen sensitive luminophores are described by: W. Xu, R. C. McDonough, B. Langsdorf, J. N. Demas, B. A. DeGraff, Oxygen sensors based on luminescence quenching: interactions of metal complexes with the polymer supports, Anal. Chem. 1994, 66, 4133–4141; S. Draxler, M. E. Lippitsch, L. Klimant, H. Kraus, O. S. Wolfbeis, Effects of polymer matrices on the time-resolved luminescence of a ruthenium complex quenched by oxygen, J. Phys. Chem. 1995, 99, 3162–3167; W. Xu, R. Schmidt, M. Whaley, J. N. Demas, B. A. DeGraff, E. K. Karikari, B. L. Farmer, Oxygen sensors based on luminescence quenching: interactions of pyrene with the polymer supports, Anal. Chem. 1995, 67, 3172–3180; P. Hartmann, W. Trettnak, Effects of polymer matrices on calibration functions of luminescent oxygen sensors based on porphyrin ketone complexes, Anal. Chem. 1996, 68, 2615–2620; and A. Mills, Lepre, Controlling the response characteristics of luminescent porphyrin plastic film sensors for oxygen, Anal. Chem. 1997, 69, 4653–4659; Amao, Y.; Asai, K.; Miyashita, T.; Okura, I., Novel optical oxygen pressure sensing materials: platinum porphyrin-styrene-trifluoroethylmethacrylate copolymer film, Chem. Lett. 1999, 1031–1032; Amao, Y.; Asai, K.; Okura, I.; Shinohara, H.; Nishide, H., Platinum porphyrin embedded in poly(1-trimethylsilyl-1-propyne) film as an optical sensor for trace analysis of oxygen, Analyst 2000, 125, 1911–1914.

Examples of such suitable polymeric materials include but are not limited to polyvinyl chloride (PVC), polystyrene (PS), poly(ethylene terephthalate) (PET), polycarbonate (PC), cellulose acetate butyrate (CAB), poly(methyl methacrylate) (PMMA), PMMA/CAB blends, fluoropolymer such as poly(styrene-co-trifluoroethyl-methacrylate) (poly-styrene-co-TFEM) and other fluoropolymers, poly(1-trimethylsilyl-2-methylacetylene), silicones, silicone blends, silicone copolymers, cation exchange membranes such as Nafion, and others.

The sensing material, when not incorporated into the barrier coating, is a thin film, suitably of a thickness from 0.05 to 1000 micrometers, particularly from 0.5 to 100 micrometers, and more particularly from 1 to 10 micrometers.

The sensing layer 18 is formed by incorporating the luminophores into the polymeric material. Incorporation of the luminophores may be carried out by dissolving a luminophore in a solution of polymeric material and then the resultant solution is applied to a substrate to form a sensing layer using various methods of thin-film deposition techniques. Solvents can be either polar or non polar, including but not limited to water, ethanol, methanol, acetone, chloroform, toluene, benzene, and hexane.

Another method for incorporation of luminophores includes dissolving a luminophore in a suitable solvent and immersing a polymer film into the luminophore solution. The polymer film swells in the solvent and some of the luminophore molecules penetrate into the swollen polymer film. Upon drying, the solvent is removed while the luminophore remains trapped in the polymer film.

For example, for oxygen permeability, a suitable chemically sensitive layer includes a polymeric material, such as silicone, polycarbonate, polymethylmethacrylate, or other similar materials, doped with an oxygen sensitive reagent, such as ruthenium complex, porphyrin complex, or other similar materials. Other suitable example of chemically sensitive layers include polymers and luminophores, such as an immobilized platinum (II) octaethylporphyrin luminophore in a polycarbonate film or in chloroform, Ru(II) complexes, combinations thereof, and other similar materials.

In another embodiment of the present invention, for example, for measurements of oxygen transport, an oxygen sensitive luminophore is incorporated into a polymer material, which is further deposited onto the acoustic wave transducer as a thin coating. An embodiment of the present invention incorporates the concept of luminescence quenching of certain luminophores upon their exposure to molecular oxygen. The luminescence intensity and lifetime of such luminophores typically decrease as the concentration of oxygen increases. This luminescence response thereby serves as a robust and predictable metric for the amount of oxygen around the luminophore. Such a luminophore is incorporable into a solid film, and such a solid-state oxygen sensor is used in one embodiment, for example, for quantitation of oxygen. See, e.g., Radislav A. Potyrailo et al., Spatially Resolved Analyte Mapping With Time-Of-Flight Optical Sensors, 17 Trends. Anal. Chem., 593–604 (1998).

Further, for example, the sensing layer may be exposed to varying concentrations of oxygen. Oxygen concentrations range from 0 to 100% by volume. Partial pressure of oxygen can range from 0 to 1 atmosphere. However, in order to accelerate penetration of oxygen, the partial pressure can be increased higher than 1 atmosphere and, depending on the equipment used, can be, for example 10, or 100 atmosphere or even higher. The sensing layer may be exposed first to the atmosphere at which the coating deposition was performed, and then to nitrogen or oxygen.

The barrier coating 20 may be any material for which a barrier property with respect to a given fluid is desired to be quantified. A suitable barrier coating may include, but is not limited to any organic material, more preferably polymers with additives, and different types of polycarbonate, polycarbonate blends, polycarbonate-polyorganosiloxane copolymers, polyetherimide resins, oxides, nitrides and oxinitrides of silicon, aluminum, zinc, boron and other metals, ceramics, polyvinyl alcohol, ethylene vinyl alcohol copolymers, polyvinyl dichloride, different types of nylon, cellophane, polypropylene, paphen phenoxy resin, high density polyethylene, low density polyethylene, poly (vinyl chloride), polyacetal, polystyrene, polyvinyl acetate, poly (butylene terphthalate), poly (ethylene terphthalate), poly (ethylene naphthalate), poly (vinylidene chloride), combinations thereof as well as other similar materials typically used to provide a barrier to transport of a given fluid. To improve barrier performance, organic polymers are often doped with numerous materials (nanocomposites, mica fillers, clays, etc.) to make organic-inorganic hybrids. The barrier coating suitably has a thickness from 0.1 nm to 100 micrometers, particularly from 1 nm to 10 micrometers, and more particularly from 10 nm to 1 micrometer. Further, the sample size of each barrier coating may vary, depending on the size of the transducer and depending on the capabilities of the detecting equipment. A suitable sample size for each of a plurality of barrier coatings may be measured by a thickness or by a mass. Further, for example, the mass of the deposited coating film may be in the range of about $1\times10^{-18}$ gram to about $1\times10^{-1}$ gram, particularly in the range of about $1\times10^{-15}$ gram to about $1\times10^{-2}$ gram, and more particularly in the range of about $1\times10^{-12}$ gram to about $1\times10^{-3}$ gram.

The plurality of fluids 28 may be a material in any phase that is generally harmful to a material covered and protected by the barrier coating. Suitable fluids usable in conjunction with the present invention include, but are not limited to oxygen; water vapor; ammonia; carbon dioxide; carbon monoxide; ethylene oxide; helium; hydrogen; hydrogen sulfide; methyl bromide; nitrogen; sulfur dioxide; fuels; alkaline and acidic solutions; water; organic solvents of different polarity; solvent mixtures; gasoline; mixtures containing hexane; a hexane/toluene mixture; ketones such as methyl amyl ketone; glycol ethers such as 2-butoxyethoanol; glycol ether esters such as ethyl-3-ethoxypropionate (EEP) and methoxy propyl acetate; toluene; methylethyl ketone (MEK); ester solvents such as ethyl acetate, butyl acetate, propyl acetate, and the like; alcohols such as butanol; 1-methdyl-2-pyrrolidinone; xylenes; and other volatile inert solvents.

The power source 22 may be any device capable of providing an oscillating potential across the electrodes 24. Suitable examples of power source 22 include, for example, a direct current battery. Additionally, the power source 22 may include additional circuitry for sequentially or simultaneously implementing the oscillating potential across one or more transducers.

The acoustic wave property measurement device 30 includes any device capable of measuring an acoustic wave property of oscillation of the transducer 12. Suitable examples of acoustic wave property measurement devices 30 include, but are not limited to, a network analyzer, a vector voltmeter, an impedance analyzer, frequency counter, a phase interferometer, and an in-phase and quadrature demodulator.

The radiation source 34 is any device capable of generating a radiation having a predetermined set of characteristics. Suitable examples of radiation source 34 include, but are not limited to, those listed in Table 1.

TABLE 1

Useful Radiation sources.

| Source | Spectral range of emission |
|---|---|
| Continuous wave sources: | |
| Xenon arc lamp | 200–1000 nm |
| Mercury arc lamp | 250–600 nm |
| Deuterium lamp | 180–420 nm |
| Tungsten lamp | 320–2500 nm |
| Light emitting diodes | different diodes cover range from 370 to 1500 nm |
| Diode lasers | different diode lasers cover range from about 400–1500 nm |
| Argon ion laser | several lines over 350–514 nm |
| Helium-neon laser | several lines over 543–633 nm |
| Krypton laser | several lines over 530–676 nm |
| Pulsed sources: | |
| Excimer lasers | |
| Nitrogen laser | 157, 193, 248, 308, 351 nm |
| Nd:YAG laser | 337 nm |
| | fundamental - 1064 nm, frequency doubled - 532 nm, |
| Ti:Sapphire laser | tripled - 355 nm, quadrupled - 266 nm |
| Dye lasers | 720–1000, frequency doubled 360–500 nm |
| | 360–990 frequency doubled 235 to 345 nm |

The detector 40 is any device capable of receiving and measuring the value of at least one characteristic of the resulting radiation 38. Suitable examples of detector 40 include, but are not limited to, a CCD camera, photomultiplier tube, avalanche photodiode, etc.

The flow cell 42 is any device having a sealable chamber for containing any of the plurality of fluids and the barrier coatings. The flow cell 42 may be sized to further contain the radiation source 34, detector 40 and other components of the system as well. If the radiation source 34 and detector 40 are maintained on the exterior of the flow cell 42, then the flow cell may be constructed of a radiation-transmissible material, at least in areas adjacent to the radiation source and the detector.

The system may further included filters (not shown) positioned between radiation source 34 and substrate 18 and/or substrate 18 and detector 40 to respectively generate or receive reference or resulting radiation with a given range of wavelengths. Filters may include any device that defines a given characteristic of the radiation. Suitable examples of filters include, but are not limited to, a monochromator (such as SLM Instruments, Inc., Urbana, Ill., Model FP-092), and/or one or more optic interference, long-pass, short-pass, or wide band-pass filters. The filter may include a liquid filter to block near-infrared radiation (such as Oriel Instruments, Stratford, Conn., Model 61945), colored-glass, a contrast-enhancement filter, a broadband filter, a dichroic filter, a laser-line filter, a long-wavepass filter, a narrowband filter, a short-wavepass filter, a neutral density filter, a tunable filter, and others. Representative manufacturers include Melles Griot, Inc., Irvine, Calif.; Kaiser Optical Systems, Inc., Ann Arbor, Mich.; Coherent Auburn Group, Auburn, Calif.; CVI Laser Corp., Albuquerque, N.Mex.; Newport Corp., Irvine, Calif.; and Omega Optical, Inc., Battleboro, Vt.

Computer 32 may be any processing device having capabilities such as inputs, outputs, software, firmware and hardware for performing the analysis discussed herein and optionally for managing the operation of the entire system. The computer 32 may be a personal computer, a workstation, a personal digital assistant, a super computer, or a processor built into or otherwise associated with one of the components of the system such as the detector.

Figure 4:
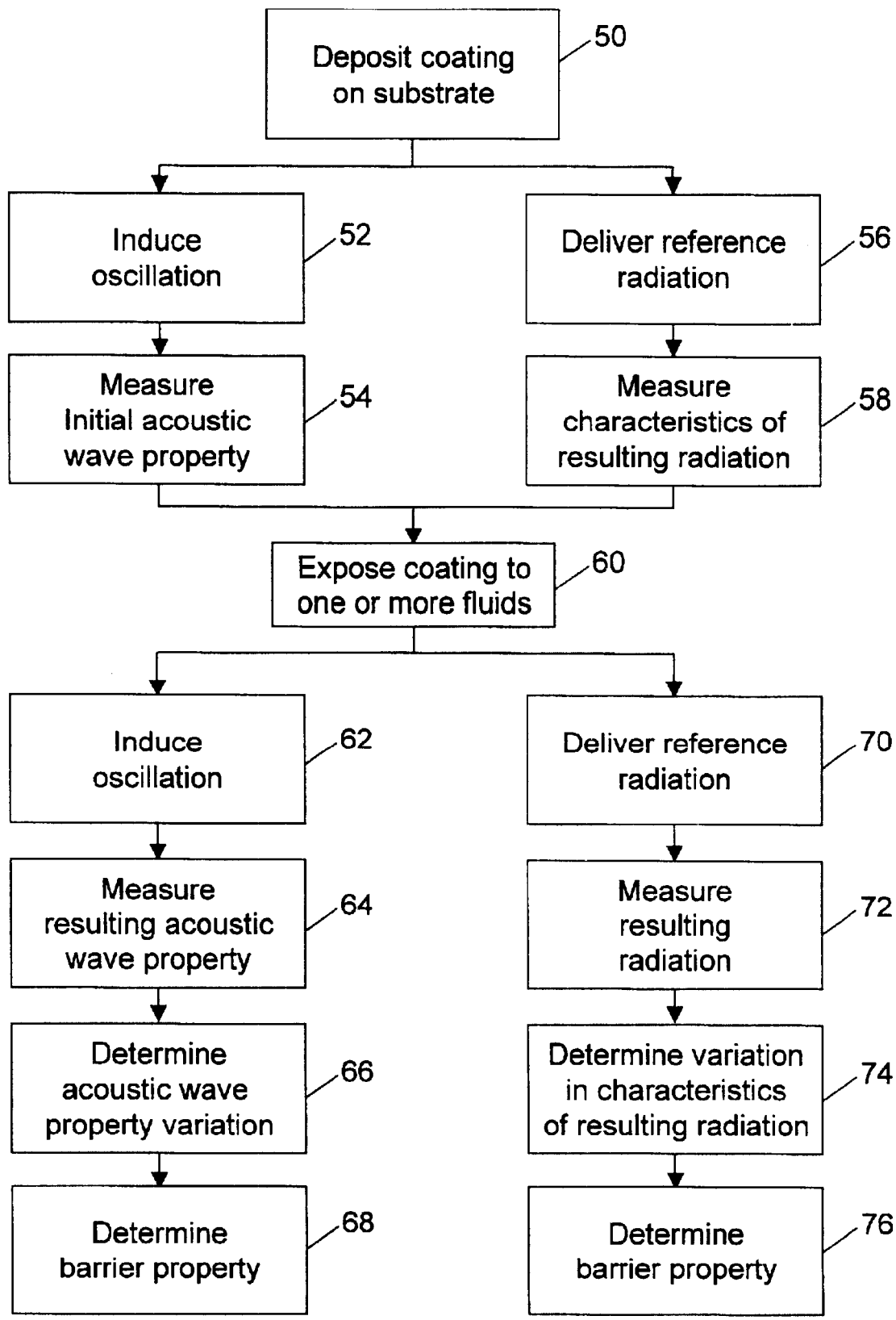
FIG. 4 is a flowchart of one embodiment of a method for determining a barrier property of a coating associated with an acoustic wave measurement technique and an optical measurement technique.

Referring to FIG. 4, either of the set-ups 10 (FIG. 1) or 14 (FIG. 2) may be utilized in a method to determine a barrier property of a coating. The coating structure is deposited on the substrate (Block 50). In the acoustic wave mode, the substrate with the deposited coating is induced to oscillate (Block 52) and this initial acoustic wave property is measured (Block 54). In the optical mode, which may occur simultaneously, the reference light is delivered to the coating structure or substrate (Block 56) and the initial characteristics of the resulting light are detected and measured (Block 58). It should be noted that the optical and acoustic wave modes may be utilized in combination or separately. Further, it should be noted that the barrier coating(s) may be spaced apart from the combination of the sensing layer and transducer. The frequency of oscillation of the acoustic wave mode does not appreciably affect the simultaneous measurements of the optical mode. Then, in both the acoustic wave and optical modes, the coating structure is exposed to one or more of the plurality of fluids for a predetermined amount of time (Block 60). The predetermined amount of time may be a set, given time period or it may be a time period that corresponds to a predetermined amount of penetration of the barrier coating by one or more of the fluids. In the acoustic wave mode, the substrate with the deposited coating is again induced to oscillate (Block 62) and this subsequent acoustic wave property is measured (Block 64). Further, any variation between the initial and subsequent acoustic wave property is determined (Block 66) and, based on the variation, a relative barrier property metric for the barrier coating with respect to one of the fluids is determined (Block 68). In the optical mode, the reference radiation is again delivered to the coating structure or substrate (Block 70) and the subsequent characteristics of the resulting radiation are detected and measured (Block 72). Further, any variation between the initial and subsequent characteristics of the resulting radiation is determined (Block 74) and, based on the variation, a relative barrier property metric for the barrier coating with respect to a different one of the fluids is determined (Block 76). It should be noted that the above methodology may be performed sequentially or continuously in either of the modes or in both modes simultaneously.

Thus, by performing the subsequent measurements in a substantially simultaneous fashion, then the barrier property of each respective barrier coating with respect to two different fluids may be determined at once. The first barrier property, with respect to a first fluid, relates to the variation in acoustic wave property associated with a change of a given material parameter in the acoustic wave mode. The second barrier property, with respect to a second fluid, relates to the variation in optical property of the resulting radiation in the optical mode.

Figure 5:
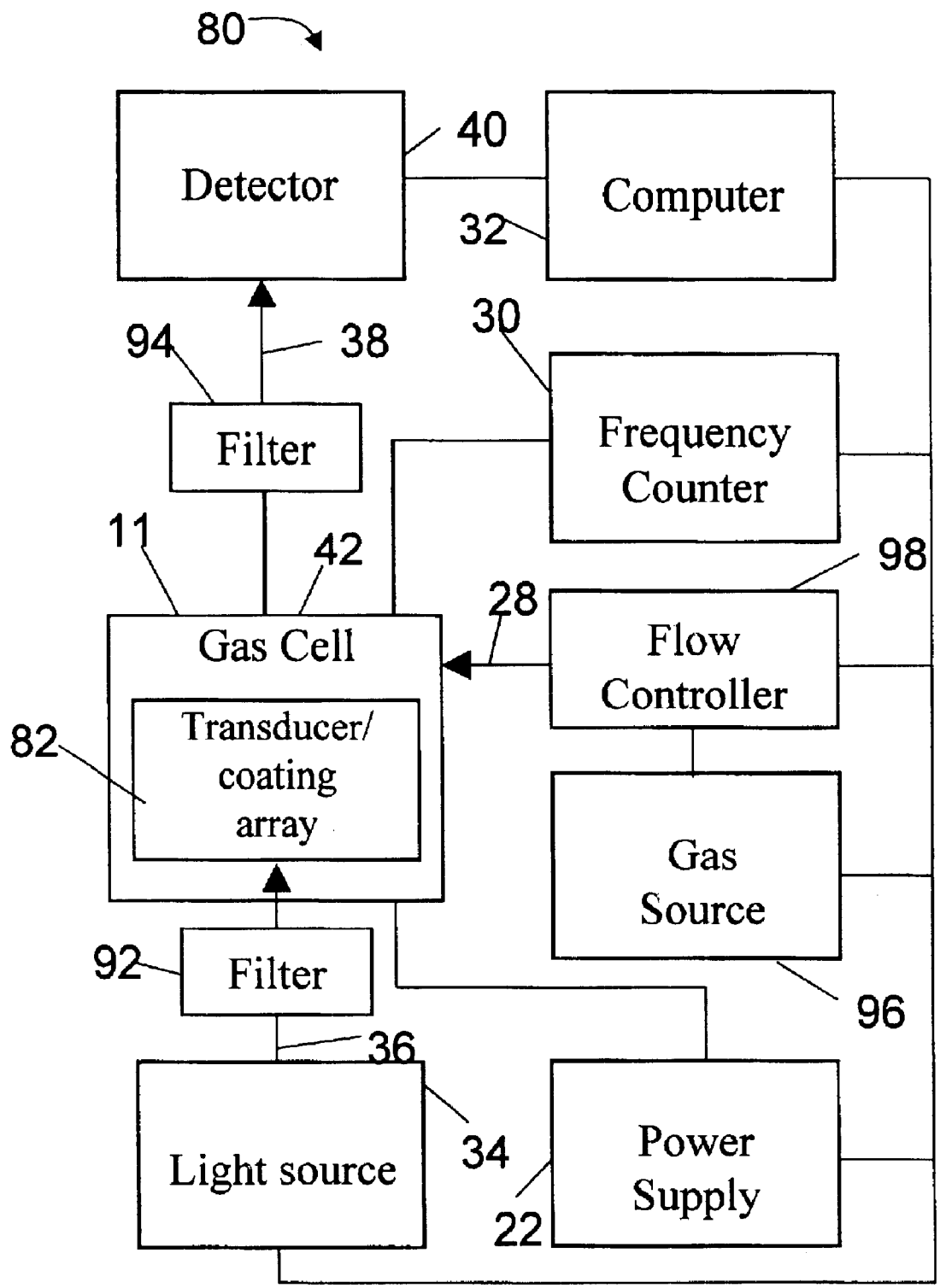
FIG. 5 is a functional diagram of the various components shown in FIGS. 1 and 2 and described in conjunction therewith.
Figure 6:
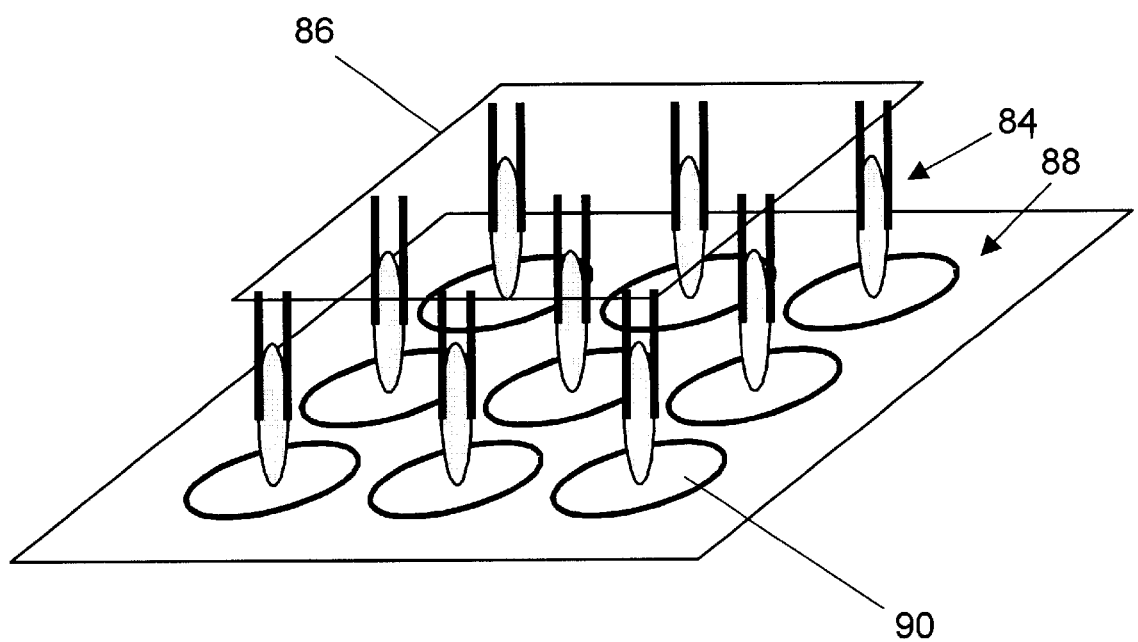
FIG. 6 is one embodiment of a system for creating and coating transducers.

Referring to FIG. 5, in one embodiment, a system 80 for barrier property screening includes a combinatorial array of coating structures 82 each one deposited onto one of an array of transducers 84 and contained within a gas flow cell 42. The combinatorial array of coating structures 82 includes a plurality of barrier coatings 20 (FIGS. 1–2) each having a unique composition, thereby enabling high throughput screening of coating compositions and their associated barrier properties. Referring to FIG. 6, in one embodiment, the array of transducers 84 may be attached to a base 86. The base 86 may be movable such that, for example, the array of transducers 84 may be simultaneously dipped in a corresponding array of wells 88, where each well 90 contains a formulation for a sensing layer 18 (FIGS. 1–2) and/or a barrier coating 20 (FIGS. 1–2) to form the coating structure 16 (FIGS. 1–2). As mentioned previously, other methods of depositing the coating structure on the transducer may also be utilized. For example, the coating structure may be sprayed onto each transducer prior to forming the array structure. Other coating procedures include, for example, spin-coating, brushing, laser deposition, vapor deposition and other deposition techniques. Additionally, the array of coating structures 82 may be cured, if required, such as by thermal or radiant curing techniques, among others.

In operation, a reference measurement of the initial characteristics of each coating structure in the array of coating structures is obtained. In the optical mode, the reference measurement is determined by the radiation source 34 projecting the reference radiation 36 toward the array of coating structures 82 and the array of transducers 84. The reference radiation 36 may be simultaneously or sequentially projected to each coating structure/transducer in the respective arrays 82 and 84. The resulting radiation 38 is detected and measured by the detector 40 to establish the initial characteristics of the resulting radiation, which is associated with the initial condition of each coating structure. The detector 40, in concert with the radiation source 34, may simultaneously or sequentially detect and measure the resulting radiation 38. Further, the initial characteristics of the resulting radiation 38 may be stored in the memory of the computer 32. It should be noted that a wavelength selection device or filter may be disposed between the radiation source 34 and the coating array to filter the reference radiation 36 into a predetermined range of wavelengths. Similarly, a wavelength selection device or filter may be disposed between the coating array and the detector 40 to filter the resulting radiation 38 into a predetermined range of wavelengths. The wavelength selection devices or filters may include, for example, monochromators, filters, liquid crystals, etc. Additionally, if the radiation is simultaneously projected and detected, then more than one light source and more than one detector may be utilized.

In the acoustic wave mode, the reference measurement is determined by the power source 22 simultaneously or sequentially supplying an oscillating potential to each transducer in the array of transducers 84. The corresponding initial acoustic wave property for each transducer with deposited coating structure, which is associated with the initial condition of each coating structure, is measured by the acoustic wave property measurement device 30 and may be stored in the computer 32. If simultaneous oscillation and measurement is performed, then more than one power source and acoustic wave property measurement device may be utilized.

After establishing the reference measurement, then the array of coating structures 82 is exposed to a predetermined number of the plurality of fluids 28 for a predetermined time period. The plurality of fluids 28 are stored within one or more fluid sources 96 and released into the gas cell 42 by a corresponding one or more flow controllers 98. The fluid sources 96 may include, for example, fluid containers or gas cylinders, and the flow controllers 98 may include, for example, valves. Additionally, the gas cell 42 may include features such as water bubblers and moisture sensors to control humidity and other types of fluid sensors to control the amount of fluid in the gas cell. The predetermined number of fluids that the array of coating structures is exposed to varies depending on the particular formulations of the coating structures and on the barrier properties being screened. For example, an inert gas such as nitrogen may be delivered to the cell through a water bubbler, thereby providing humidity or moisture. At the same time, oxygen may also be delivered to the cell. Thus, the barrier coatings are simultaneously exposed to moisture and oxygen, and these respective barrier properties may be simultaneously measured. The predetermined time period also may vary depending on the particular formulations of the coating structures and on the barrier properties being screened. Suitable predetermined time periods may range from about 1 millisecond to about 1 year, or from about 10 milliseconds to about 1 month, preferably from about 10 milliseconds to about 1 week, more preferably from about 100 milliseconds to about 1 day, and most preferably from about 1 second to about 1 hour. Alternately, the predetermined time period may be an uncertain time period that concludes with a given measured response of a coating structure. For example, the time period of the exposure may be continuous until the fluids have penetrated each coating structure in the array of coating structures to predetermined measurable degree, such as an amount of penetration that would indicate failure of the barrier coating.

At predetermined intervals or continuously throughout the exposure time period, a subsequent measurement of the subsequent characteristics of each coating structure in the array of coating structures 82 is simultaneously obtained in the optical and acoustic wave modes. In both the optical and acoustic wave mode, the subsequent measurement is obtained as described above for the initial measurement. Then, the initial and subsequent measurements are compared and the variation in measurements is determined for each coating structure in the array 82. For example, the computer 32 may include software for comparing these measurements and determining the variation in measurement. The relative performance of each coating structure is determined, based on the variation in measurements, where the variation in measurement associated with each of the optical and acoustic wave modes is associated with a different one of the plurality of fluids. Preferably, each of the plurality of fluids for which a simultaneous barrier property measurement is desired has a different affect simultaneously measurable via the acoustic wave mode and/or the optical mode. As mentioned above, for example, the optical mode may measure oxygen permeability while the acoustic mode measures moisture permeability. Each mode may measure more than one barrier property if the measurable effects are exclusive within the given mode.

Again, for example, the computer 32 may include software for comparing the relative performance of each coating structure. Further, the variation in measurement for each mode may be correlated to a barrier property for each of the coating structures with respect to a different one of the fluids. Once again, the computer 32 may include software for performing the correlation of the measurement variation with a barrier property. Thus, the transmission rate characteristics, or barrier properties, of each individual coating within an array of barrier coatings are simultaneously measurable with respect to different ones of the plurality of fluids exposed to the array.

Figure 7:
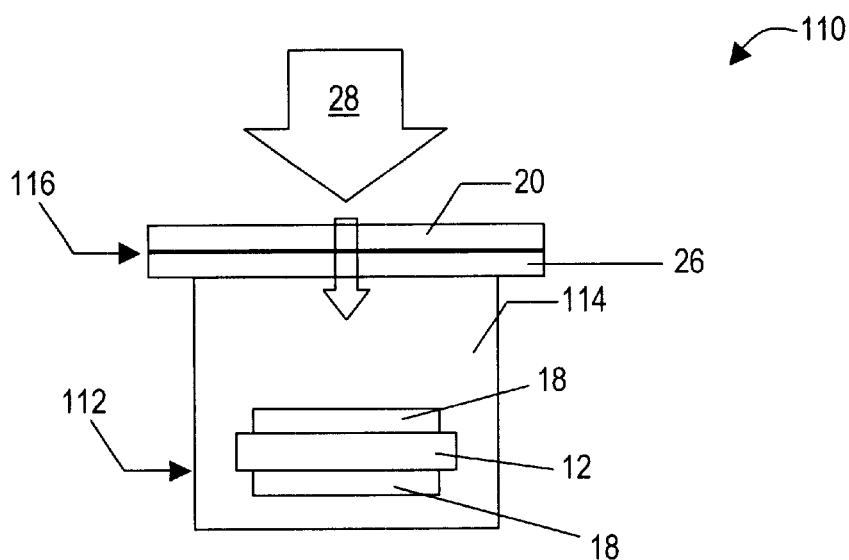
FIG. 7 is a schematic diagram of one embodiment of one of the channels of a acoustic wave optical sensor array for measurement of transport of plurality of fluids through a barrier coating deposited directly onto a substrate of interest.

In another embodiment, referring to FIG. 7, a set-up 110 may be utilized to measure, for example, moisture transport of an array of barrier coatings. A sensor 112 is arranged in proximity to the barrier coating in a low-dead-volume gas-impermeable cell 114. A barrier coating 20 is deposited onto a substrate 26 and seals the cell 114. One side of the coating/substrate structure 11 6 is exposed to a fluid or fluids 28 and the acoustic wave and/or optical signals of the sensor 112 are monitored to detect transport of fluids through the barrier coating 20 and substrate 26. The sensor layer or layers 18 serve to absorb the fluids 28 and generate the acoustic wave and/or optical signals. It should noted that although FIG. 7 shows a dual mode transducer, a single mode (acoustic wave or optical) transducer may instead be utilized. Further, it should be noted that the set-up shown in FIG. 7 may be further utilized to determine barrier properties of a coating with respect to other fluids. It should also be noted that the sensor may include an acoustic wave sensor separate from, as opposed to integral with, an optical sensor.

An acoustic wave sensor has a sensing layer sensitive to one or more of the fluids transported through the barrier coating. The change in the acoustic wave property of the transducer is associated with the changing material parameters of the oscillating crystal due to the permeation of one or more fluids into the sensing layer. These material parameters include the change in property of the deposited material such as density, viscosity, mass, and crystallinity. These properties can be measured separately by monitoring a variety of parameters from a one- or two-port acoustic-wave device. These measured parameters include fundamental oscillation frequency, harmonic oscillation frequency, impedance phase and magnitude of one-port devices, impedance phase and attenuation of two-port devices, wave velocity and wave attenuation, capacitance, and conductance.

An optical sensor can analyze any optical property including absorbance (e.g., ultraviolet (UV), visible, infrared), luminescence, Raman scattering, refractive index, or a combination of these properties. The measurement techniques can incorporate any known configuration to analyze bulk or surface properties of a measured medium which can include both the sensing material deposited onto a transducer and the fluid transported into the cell 114. For example, a bulk optical property of a medium can be measured using a single-ended probe, a 180-degrees transmission setup, a 90-degrees scatter or emission setup or any other system suitable for bulk measurements. See for example, Ingle, J. D., Jr.; Crouch, S. R. Spectrochemical Analysis; Prentice Hall: Englewood Cliffs, N. J., 1988, chapters 13, 15, and 16; Handbook of Instrumental Techniques for Analytical Chemistry; Settle, F. A., Ed.; Prentice Hall PTR: Upper Saddle River, N.J., 1997, chapters 16, 25, and 26.

Analysis of surface properties can be also performed using a variety of known optical techniques. These include evanescent-wave techniques such as evanescent-wave absorbance, evanescent-wave luminescence, surface plasmon resonance, evanescent-wave cavity ring-down spectroscopy, and others. Analysis can be performed of the optical changes of a sensing layer upon interactions with the fluids in cell and/or directly fluids 28 in contact with the surface of the sensor. See for example, Potyrailo, R. A.; Hobbs, S. E.; Hieftje, G. M., Optical waveguide sensors in analytical chemistry: today's instrumentation, applications and future development trends, Fresenius" J. Anal. Chem. 1998,362, 349–373; Pipino, A. C. R.; Hudgens, J. W.; Huie, R. E., Evanescent wave cavity ring-down spectroscopy with a total-internal-reflection minicavity, Rev. Sci. Instrum. 1997, 68, 2978–2989; Vasudev, R.; Usachev, A.; Dunsford, W. R., Detection of toxic compounds by cavity ring-down spectroscopy, Environ. Sci. Technol. 1999, 33, 1936–1939.

Thus, including the embodiment of FIG. 7 with the other embodiments, a barrier coating may be positioned in a spaced apart relationship with a sensor and directly applied to a substrate of interest, or deposited on a sensor with or without a sensing layer and including a substrate of interest, and optical and acoustic wave techniques may be utilized to determined a barrier property of the coating with respect to one or more fluids exposed to the coating.

For highly sensitive measurements of moisture transported through a barrier film, poly(N-vinylpyrrolidone) was used as a sensing material deposited onto the transducer. A 10-MHz TSM transducer was dip-coated with poly(N-vinylpyrrolidone) and positioned in a flow through cell. Different levels of relative humidity were generated by bubbling dry nitrogen through water at different flow rates and further diluting the moist vapor with dry nitrogen. A commercially available relative humidity meter was used as a reference for calibration.

Figure 8:
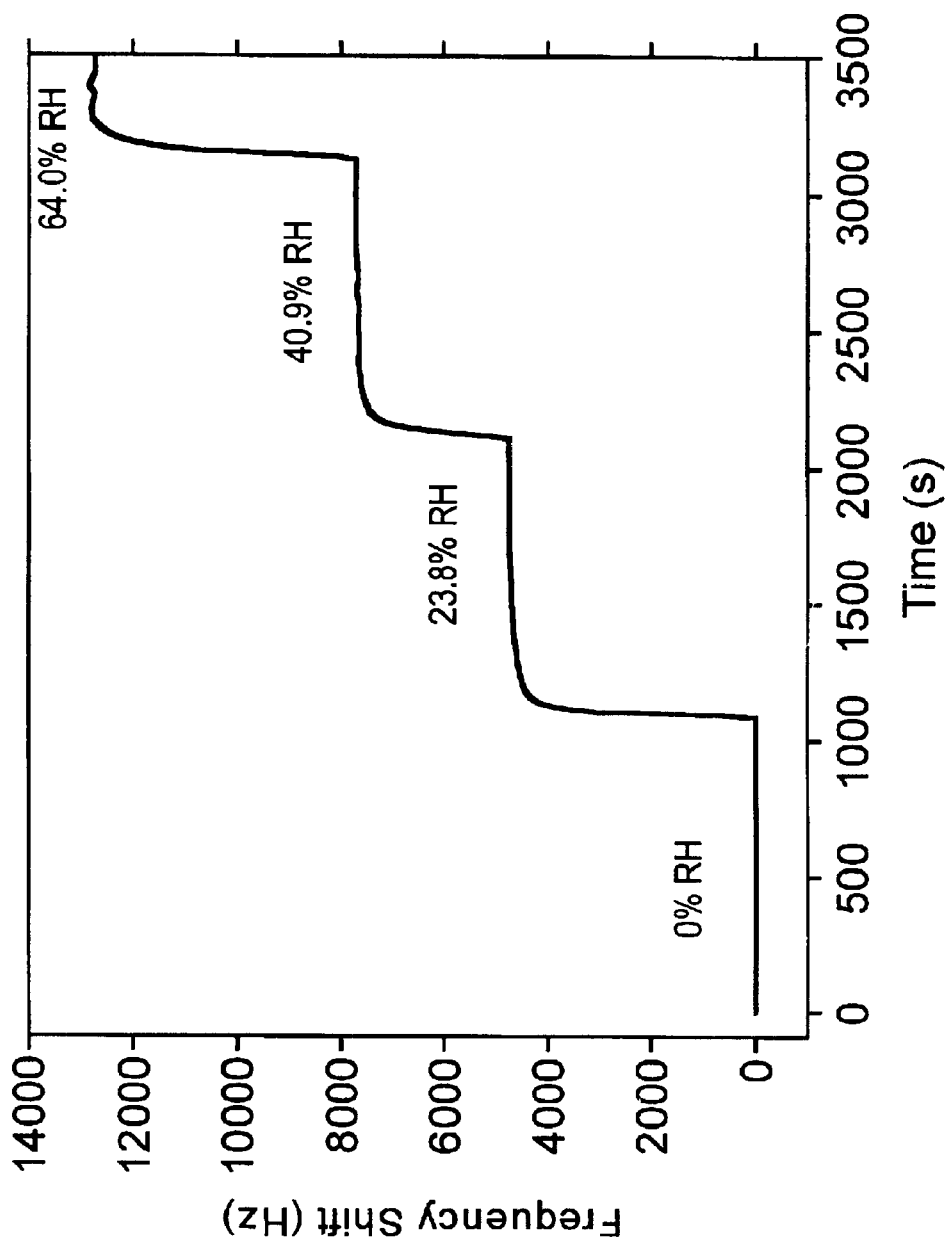
FIG. 8 is a graph of a dynamic response of one embodiment of a TSM device coated with poly(N-vinylpyrrolidone) sensor material exposed to increasing amounts of relative humidity (RH) in air.
Figure 9:
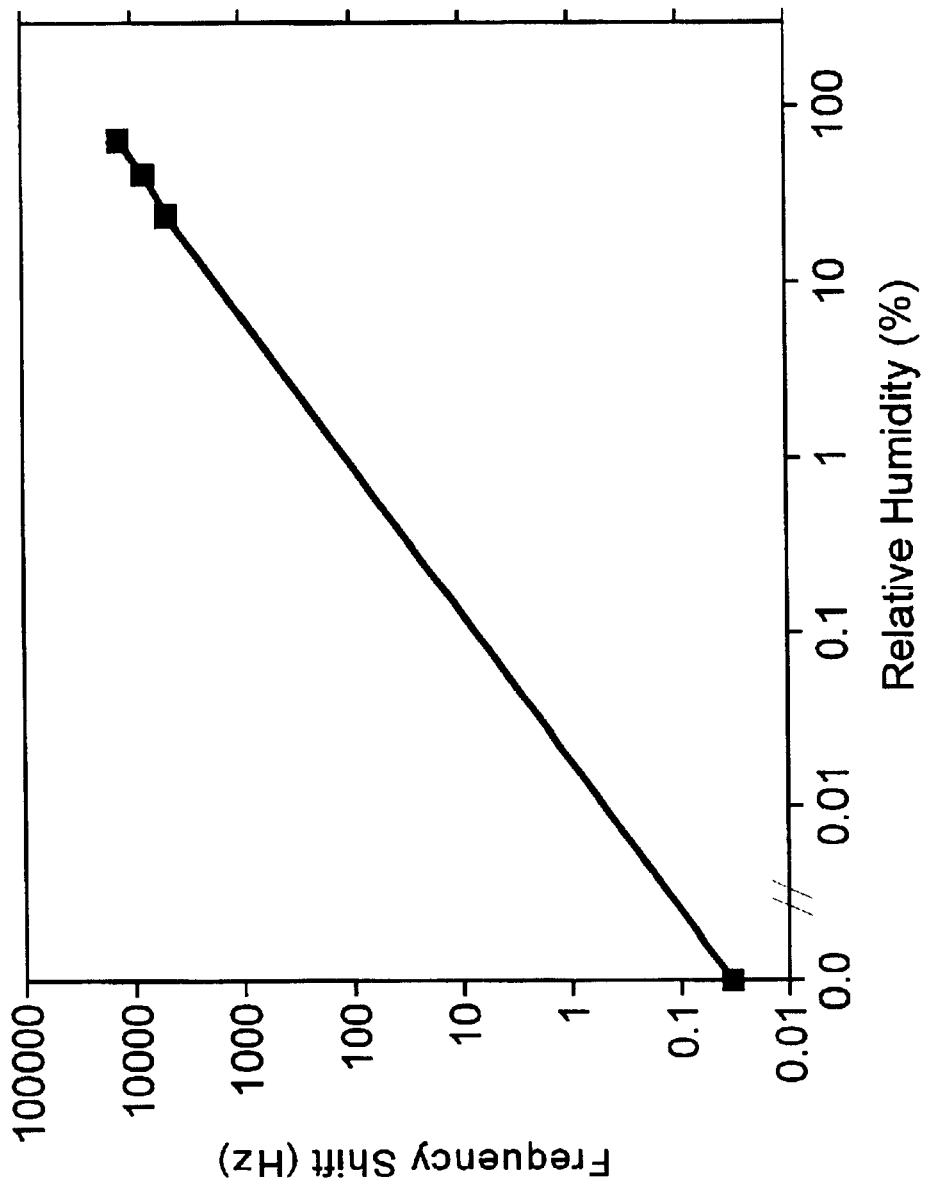
FIG. 9 is a graph of a dynamic range of one embodiment of a TSM device coated with poly(N-vinylpyrrolidone) sensor material in measuring moisture in air.

Poly(N-vinylpyrrolidone) is known to be highly sensitive to polar vapors. See for example, Ranucci, E.; Ferruti, P.; Opelli, P.; Ferrari, V.; Marioli, D.; Taroni, A., Poly (N-vinylpyrrolidone) as moisture-sorbing material for relative humidity sensors, Sens. Mater. 1994, 5, 221–229; Freud, M. S.; Lewis, N. S., A chemically diverse conducting polymer-based "electronic nose," Proc. Natl. Acad. Sci. USA 1995, 92, 2652–2656; Vaid, T. P.; Burl, M. C.; Lewis, N. S., Comparison of the performance of different discriminant algorithms in analyte discrimination tasks using an array of carbon black-polymer composite vapor detectors, Anal. Chem. 2001, 73, 321–331; Matsuguchi, M.; Umeda, S.; Sadaoka, Y.; Sakai, Y., Characterization of polymers for a capacitive-type humidity sensor based on water sorption behavior, Sens. Actuators B 1998, 49, 179–185. FIGS. 8 and 9 depict the response of the TSM device coated with poly(N-vinylpyrrolidone) film to increasing amounts of moisture in air. This data illustrates not only rapid response of polymer-coated sensor to humidity (FIG. 8), but also an extremely broad dynamic range of the sensor response (FIG. 9). Upon the increase of relative humidity from 0 to 64%

RH, the sensor response (frequency shift) was more than 5.5 orders of magnitude taking into an account a 0.05-Hz measurement noise level.

Oxygen barrier properties may be evaluated using, for example, phosphorescent, chemiluminescent, and calorimetric oxygen sensitive reagents. Further, materials with high oxygen solubility are suitable as oxygen-sensing materials upon immobilization of certain luminophores. Styrene-trifluoroethylmethacrylate copolymer and poly(1-trimethylsilyl-1-propyne) or poly (1-trimethylsilyl-2-methylacetylene) are known to be suitable oxygen sensing materials. See for example, Amao, Y.; Asai, K.; Miyashita, T.; Okura, I., Novel optical oxygen pressure sensing materials: platinum porphyrin-styrene-trifluoroethylmethacrylate copolymer film, Chem. Lett. 1999, 1031–1032; Amao, Y.; Asai, K.; Okura, I.; Shinohara, H.; Nishide, H., Platinum porphyrin embedded in poly(1-trimethylsilyl-1-propyne) film as an optical sensor for trace analysis of oxygen, Analyst 2000, 125, 1911–1914.

These polymers were used with platinum porphyrins such as (Pt(II) octaethylporhine and (Pt(II)O) Pt(II)meso-tetra (pentafluoirophenyl)porphine (Pt(II)M), both from Porphyrin Products, Inc., Logan, Utah as oxygen-sensitive luminophores. Sensor materials were prepared with 0.1–10 $\mu$M concentrations of the luminophores in toluene solutions of poly(1-trimethylsilyl-2-methylacetylene). About 20-microliters of a given solution was pipetted into a quartz substrate dried in air. Different oxygen concentrations were generated by diluting 100% dry oxygen with dry nitrogen using high precision mass flow controllers.

Figure 10:
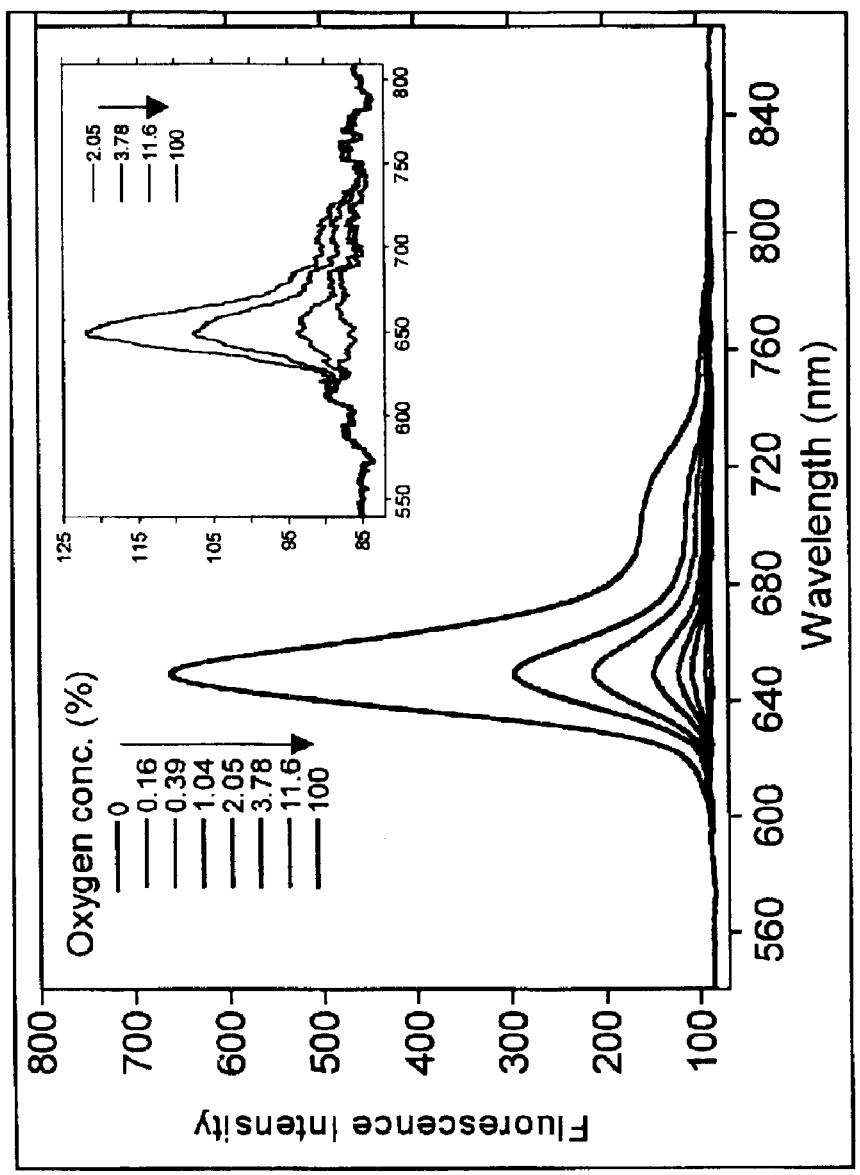
FIG. 10 is a graph of luminescence spectra of one embodiment of a Pt(II)meso-tetra(pentafluoirophenyl) porphine in poly(1-trimethylsilyl-2-methylacetylene) upon exposure to different oxygen concentrations at an excitation wavelength of 392 nm.
Figure 11:
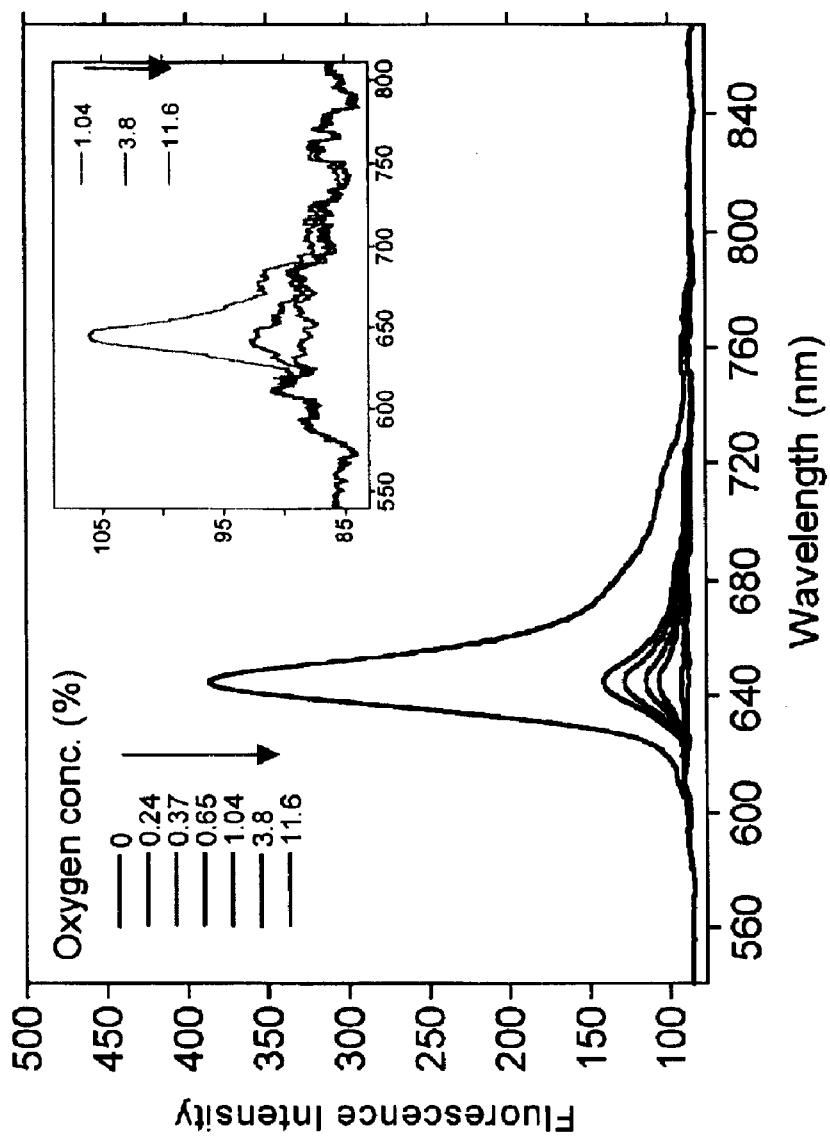
FIG. 11 is a graph of luminescence spectra of one embodiment of Pt(II) octaethylporhine in poly(1-trimethylsilyl-2-methylacetylene) upon exposure to different oxygen concentrations at an excitation wavelength of 392 nm.

Luminescence spectra of these materials upon exposure to different oxygen concentrations are shown in FIGS. 10 and 11. These spectra illustrate high oxygen-quenching efficiency and a low luminescence background.

Figure 12:
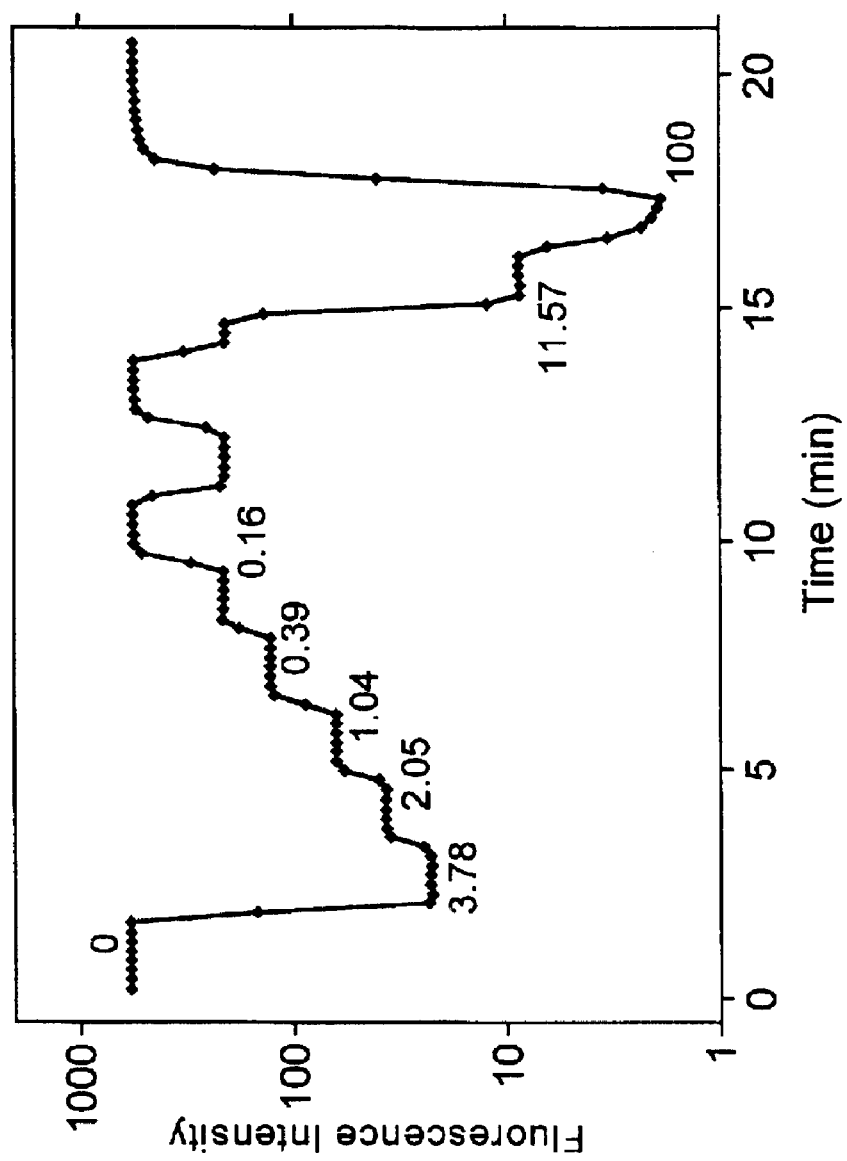
FIG. 12 is a graph of a dynamic response of one embodiment of Pt(ll)meso-tetra (pentafluoirophenyl)porphine in poly(1-trimethylsilyl-2-methylacetylene) upon exposure to different oxygen concentrations at an excitation wavelength of 392 nm and an emission wavelength of 645 nm, where the numbers represent oxygen concentration (vol. %)
Figure 13:
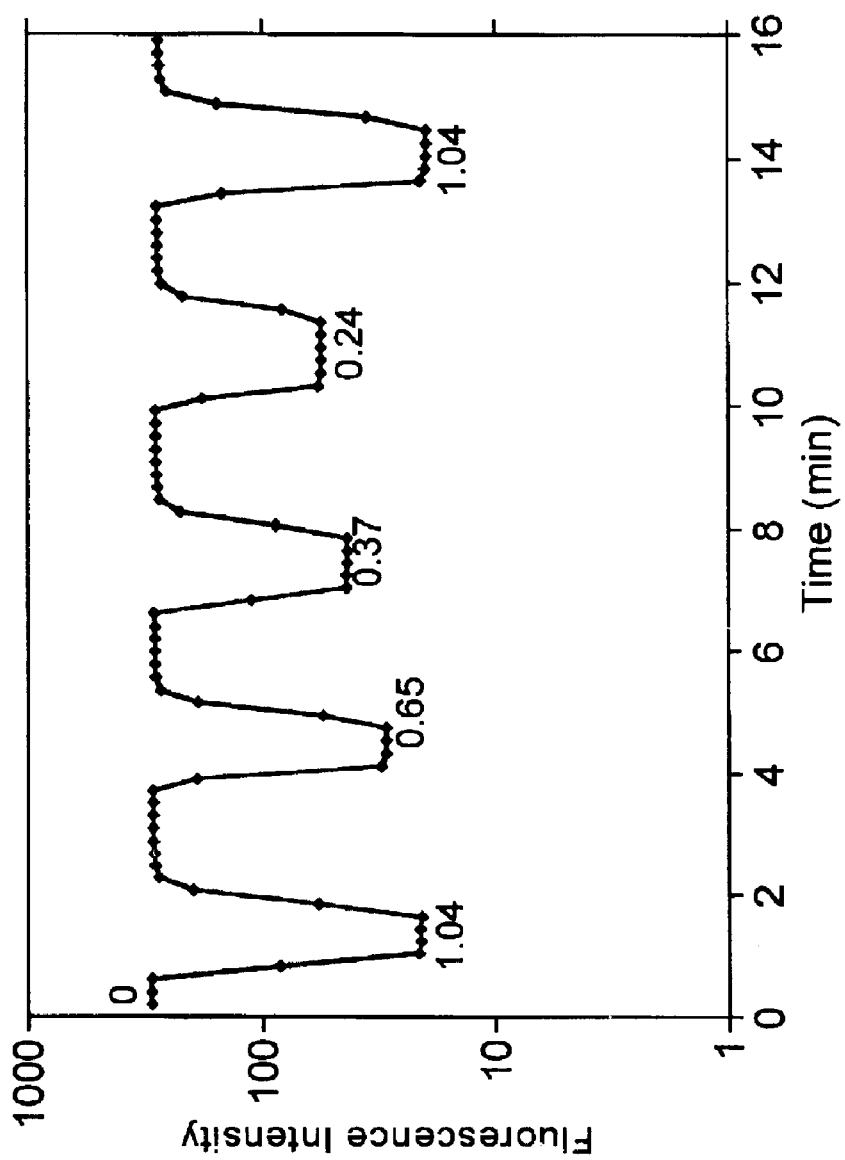
FIG. 13 is a graph of a dynamic response of one embodiment of Pt(II) octaethylporhine in poly(1-trimethylsilyl-2-methylacetylene) upon exposure to different oxygen concentrations at an excitation wavelength of 392 nm and an emission wavelength of 645 nm, where the numbers represent oxygen concentration (vol. %)

To evaluate signal stability upon extended exposure of the sensor materials to the excitation radiation (392 nm) and to assess the dynamic response of the sensors, the luminescence intensity was monitored at 645 nm as a function of exposure time at different oxygen concentrations. The background-corrected results of these dynamic experiments are presented in FIGS. 12 and 13.

Figure 14:
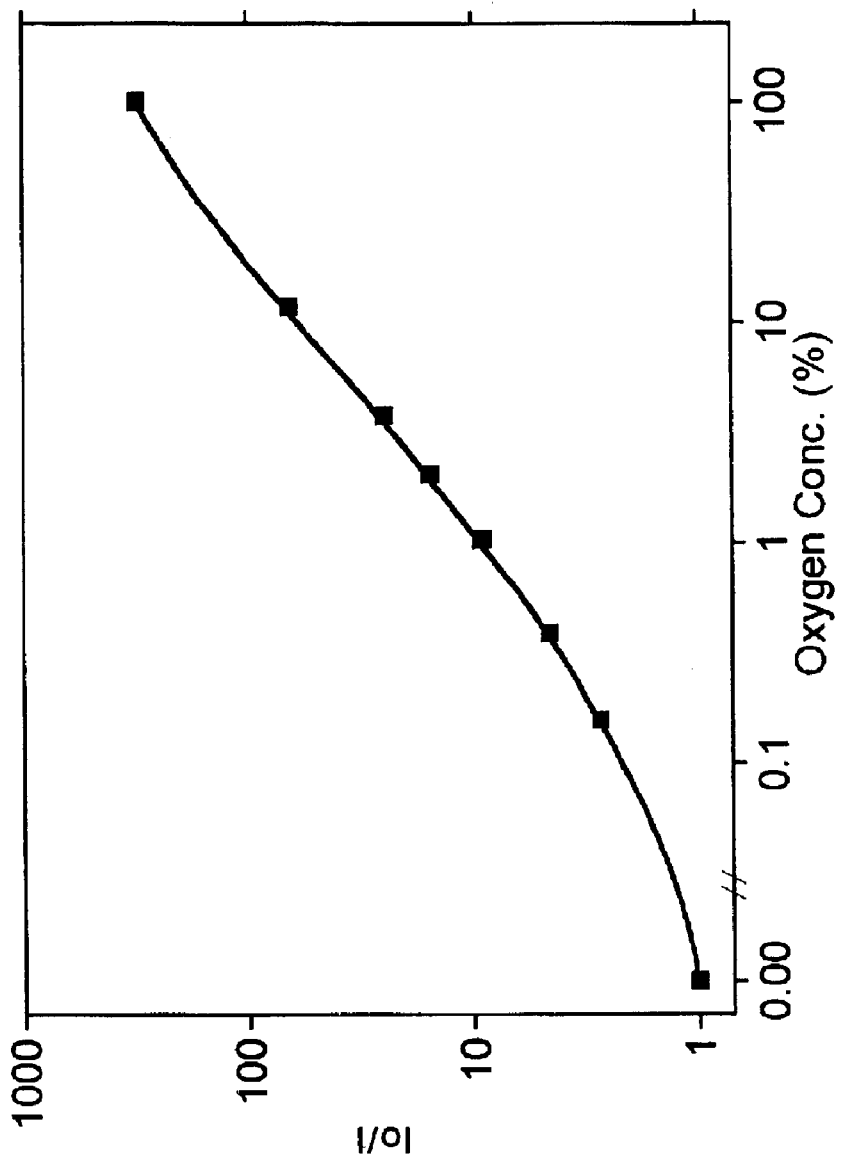
FIG. 14 is a log—log Stern-Volmer plot for an embodiment of a Pt(II)meso-tetra (pentafluoirophenyl)porphine in poly(1-trimethylsilyl-2-methylacetylene) sensing material over broad concentration range of oxygen (from 0 to 100 vol. %)
Figure 15:
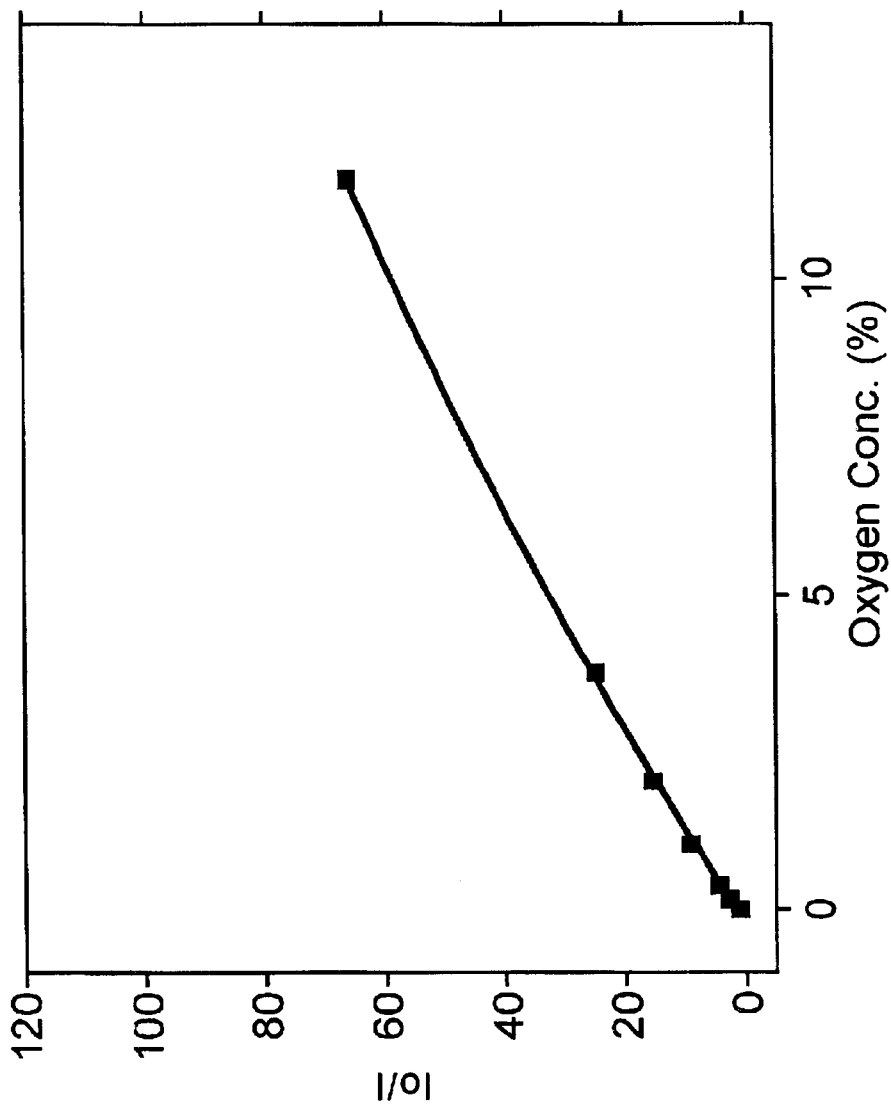
FIG. 15 is a Stern-Volmer plot for an embodiment of a Pt(II)meso-tetra (pentafluoirophenyl)porphine in poly(1-trimethylsilyl-2-methylacetylene) sensing material over an oxygen concentration range up to about 12 vol. %.
Figure 16:
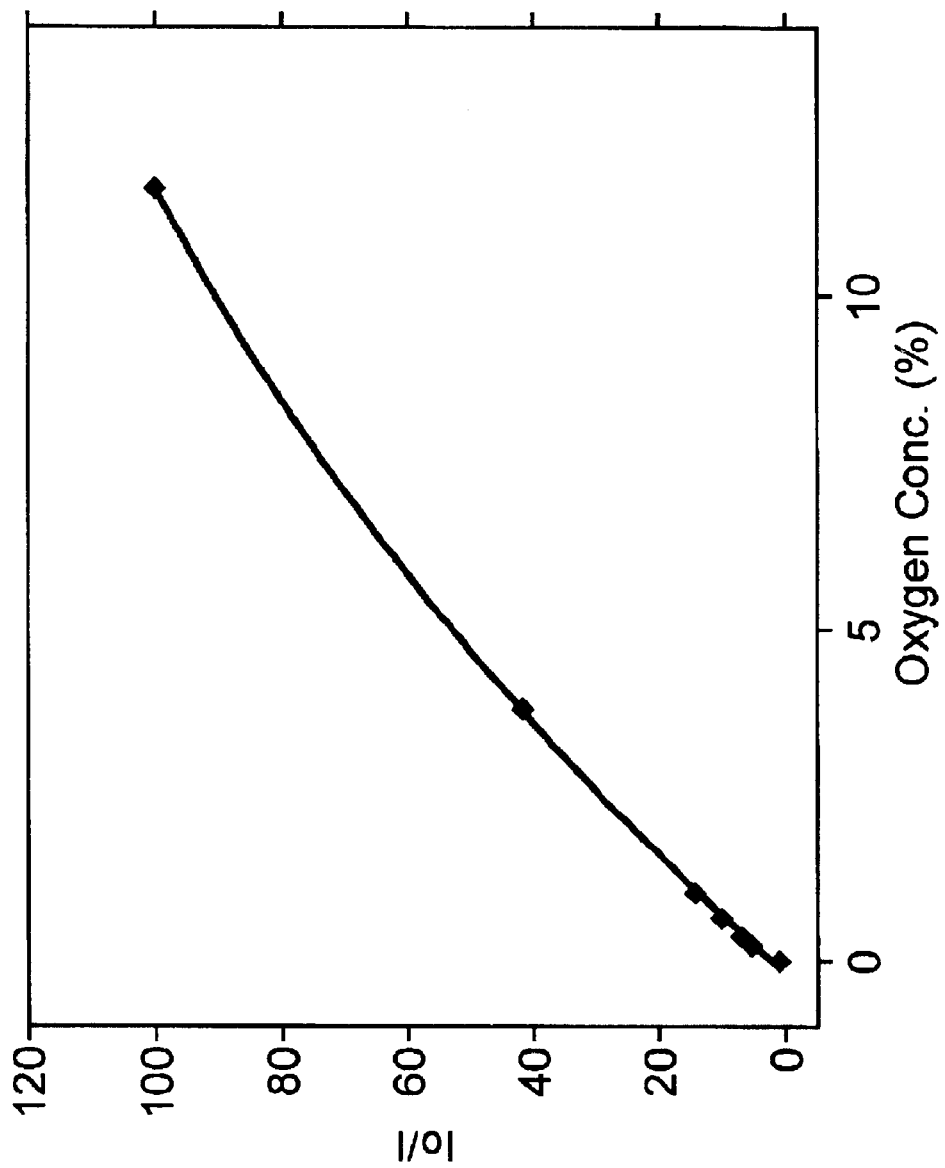
FIG. 16 is a Stern-Volmer plot for an embodiment of a Pt(II)octaethylporhine in poly(1-trimethylsilyl-2-methylacetylene) sensing material over an oxygen concentration range up to about 12 vol. %.

The Stern-Volmer plots are presented in FIGS. 14, 15 and 16. Both materials have only a slight non-linearity in response to oxygen at high concentrations. This is an important advantage of these materials as compared to other types of highly sensitive materials such as silica gels. Silica gel-based sensor response typically saturates at medium-high oxygen concentrations.

Example embodiments of the present invention have now been described. It will be appreciated that these examples are merely illustrative of the invention, and they should not be construed as limiting the invention. Many variations and modifications will be apparent to those skilled in the art.

What is claimed is:

1. A system for determining barrier properties of a barrier coating, comprising:
   at least one dual-mode transducer comprising at least one sensor, the at least one sensor comprising at least one material responsive to interactions with a plurality of fluids;
   at least one barrier coating associated with each sensor, such that said barrier coating is positioned between said sensor and said fluids to thereby modify the interaction of said sensor with said fluids, wherein said barrier coating at least partially prevents a fluid from interacting with said at least one sensor; and
   wherein each sensor has initial characteristics and subsequent characteristics each associated with the barrier properties of the coating with respect to each of a plurality of fluids, where the initial characteristics correspond to the barrier coating properties prior to exposure to any of the plurality of fluids and the subsequent characteristics correspond to the barrier coating properties after exposure to at least two of a plurality of fluids, the initial characteristics for each barrier coating comprising an initial optical property and an initial acoustic wave property, and the subsequent characteristics of each barrier coating comprising a subsequent optical property and subsequent acoustic wave property;
   wherein the initial and subsequent acoustic wave properties correlate to the density, viscosity, mass, or crytallinity of the sensor material before and after, respectively, exposure of the coating to the plurality of fluids, and the initial and subsequent optical properties correspond to the ability of the sensor to respond to radiation before and after, respectively, exposure of the coating to the plurality of fluids;
   an optical characteristic measurement device for measuring the initial optical property and subsequent optical property associated with each barrier coating;
   an acoustic wave property measurement device for measuring the initial acoustic wave property and the subsequent acoustic wave property associated with each barrier coating; and
   a computer for determining a first barrier property and a second barrier property of each barrier coating, the first barrier property with respect to one of the plurality of fluids, the second barrier property with respect to a second of the plurality of fluids, the first barrier property and the second barrier property based on the variation between the initial characteristics and subsequent characteristics associated with both the optical properties and the acoustic wave properties of each barrier coating.

2. The system of claim 1, wherein the acoustic wave sensor further produces a first acoustic wave property and a second acoustic wave property, where the first acoustic wave property corresponds to the initial characteristics of the barrier coating, and where the second acoustic wave property corresponds to the subsequent characteristics of the barrier coating.

3. The system of claim 1, wherein the initial optical property and subsequent optical property associated with each barrier coating are selected from the group consisting of absorbance, luminescence, refractive index, scattering, polarization and a combination thereof.

4. The system of claim 3, wherein the sensor comprises a total-internal reflection element, and wherein the initial optical property and the subsequent optical property associated with each barrier coating are determined from a light propagated within the total-internal reflection element.

5. The system of claim 1, wherein the barrier coating comprises a material selected from the group consisting of an organic material, a polymer with additives, an organic-inorganic hybrids, a polycarbonate, polycarbonate blends, polycarbonate-polyorganosiloxane copolymers, polyetherimide resins, oxides, nitrides and oxinitrides of silicon, aluminum, zinc, boron and other metals, ceramics, polyvinyl alcohol, ethylene vinyl alcohol copolymers, polyvinyl dichloride, nylon, cellophane, polypropylene, paphen phenoxy resin, high density polyethylene, low density polyethylene, poly (vinyl chloride), polyacetal, polystyrene, polyvinyl acetate, poly (butylene terphthalate), poly (ethylene terphthalate), poly (ethylene naphthalate), poly (vinylidene chloride), and combinations thereof.

6. The system of claim 1, wherein the sensor comprises a sensing layer.

7. The system of claim 6, wherein the sensing layer comprises a material that does not change the properties of the coating layer and that interacts with the plurality of fluids in a manner that may be measured.

8. The system of claim 7, wherein the sensing layer comprises an organic or inorganic luminescent or calorimetric material disposed in a matrix.

9. The system of claim 1, wherein the plurality of fluids are selected from the group consisting of oxygen; water vapor; ammonia; carbon dioxide; carbon monoxide; ethylene oxide; helium; hydrogen; hydrogen sulfide; methyl bromide; nitrogen; sulfur dioxide; fuels; alkaline and acidic solutions; water; organic solvents of different polarity; solvent mixtures; gasoline; mixtures containing hexane; a hexane/toluene mixture; ketones; glycol ethers; glycol ether esters; toluene; methylethyl ketone (MEK); ester solvents, butyl acetate, propyl acetate; alcohols; 1-methyl-2-pyrrolidinone; xylenes; and a volatile inert solvent; and combinations thereof.

10. The system of claim 1, wherein the first barrier property corresponds to one of the two of the plurality of fluids based on the variation between the initial optical property and subsequent optical property associated with each barrier coating.

11. The system of claim 10, wherein the second barrier property corresponds to the other of the two of the plurality of fluids based on the variation between the initial acoustic wave property and subsequent acoustic wave property associated with each barrier coating.

12. The system of claim 1, wherein the initial optical property and the corresponding initial acoustic wave property are simultaneous measurements.

13. The system of claim 1, wherein the subsequent optical property and the corresponding subsequent acoustic wave property of each barrier coating are simultaneous measurements.

14. The system of claim 1, wherein the at least one sensor further comprises a plurality of sensors; and where the at least one barrier coating comprises a plurality of barrier coatings, wherein the plurality of barrier coatings comprise a combinatorial array.

15. The system of claim 14, wherein the computer further determines the relative performance of each of the first barrier property and second barrier property for each of the plurality of barrier coatings.

16. A system for determining barrier properties of a barrier coating, comprising:
at least one dual-mode transducer comprising a plurality of sensors each having at least one external surface comprising at least one material responsive to interactions with a plurality of fluids;
a plurality of barrier coatings, wherein said barrier coatings at least partially prevent a fluid from interacting with at least one of said sensors;
and wherein each of the plurality of barrier coatings is associated with a corresponding one of the plurality of sensors, such that each of the plurality of barrier coatings is positioned between a corresponding one of the plurality of sensors and said fluids to thereby modify the interaction of said sensor with said fluids, with each sensor having initial characteristics and subsequent characteristics each associated with the barrier properties of the barrier coating with respect to each of a plurality of fluids, where the initial characteristics correspond to the barrier coating properties prior to exposure to any of the plurality of fluids and the subsequent characteristics correspond to the barrier coating properties after exposure to at least two of a plurality of fluids, the initial characteristics for each sensor comprising an initial optical property and an initial acoustic wave property, and the subsequent characteristics of each sensor comprising a subsequent optical property and a subsequent acoustic wave property;
wherein the initial and subsequent acoustic wave properties correlate to the density, viscosity, mass, or crytallinity of the sensor material before and after, respectively, exposure of the coating to the plurality of fluids, and the initial and subsequent optical properties correspond to the ability of the sensor to respond to radiation before and after, respectively, exposure of the coating to the plurality of fluids;
an optical characteristic measurement device for measuring the initial optical property and the subsequent optical property associated with each of the plurality of barrier coatings;
an acoustic wave property measurement device for measuring the initial acoustic wave property and the subsequent acoustic wave property associated with each of the plurality of barrier coatings;
a processing device for determining a first barrier property and a second barrier property of each of the plurality of barrier coatings, the first barrier property with respect to one of the plurality of fluids, the second barrier property with respect to a second of the plurality of fluids, the first barrier property and the second barrier property based on the variation between the initial characteristics and subsequent characteristics associated with both the optical properties and the acoustic wave properties of each barrier coating; and
wherein the subsequent optical property and the corresponding subsequent acoustic wave property associated with each barrier coating are simultaneous measurements.

17. The system of claim 16, wherein the initial optical property or the subsequent optical property is based, respectively, on a reference radiation or a resulting radiation having an intensity in the range of about a single photon to about 1 kilowatt.

18. The system of claim 16, wherein the initial optical property or the subsequent optical property is based, respectively, on a reference radiation or a resulting radiation having a wavelength in the range of about 10 nanometers to about 50 micrometers.

19. The system of claim 16, wherein the initial optical property or the subsequent optical property is based, respectively, on a reference radiation or a resulting radiation having a polarization state in the range of about 0 degrees to about 360 degrees.

20. The system of claim 16, wherein the initial optical property or the subsequent optical property is based, respectively, on a reference radiation or a resulting radiation having a phase difference in the range of about 0.001 to about 10,000 wavelengths of probe radiation.

21. The system of claim 16, wherein the initial optical property or the subsequent optical property is based, respectively, on a reference radiation or a resulting radiation having a luminescence lifetime in the range of about 10 picoseconds–1000 seconds.

22. The system of claim 16, wherein the initial optical property or the subsequent optical property is based, respectively, on a reference radiation or a resulting radiation having a time delay in the range of about 1 femtosecond–1000 seconds.

23. The system of claim 16, wherein the sensor comprises a total-internal reflection element, and wherein the initial optical property and subsequent optical property of each barrier coating are determined from a light propagated within the total-internal reflection element.

24. The system of claim 16, wherein the sensor comprises a total-internal reflection element, and wherein the initial optical property and subsequent optical property of each barrier coating are determined from a light propagated toward an external surface total-internal reflection element.

25. The system of claim 16, wherein the first barrier property corresponds to one of the two of the plurality of fluids based on the variation between the initial characteristics and subsequent characteristics associated with the optical properties of each barrier coating.

26. The system of claim 25, wherein the second barrier property corresponds to the other of the two of the plurality of fluids based on the variation between the initial characteristics and subsequent characteristics associated with the acoustic wave property of each barrier coating.

27. The system of claim 16, wherein the computer further determines the relative performance of each of the first barrier property and second barrier property for each of the plurality of barrier coatings.

28. A method for screening for barrier properties of a barrier coating, comprising:

positioning at least one barrier coating between a plurality of fluids and at least one sensor wherein said sensor comprises at least one material responsive to interactions with a plurality of fluids, and wherein said barrier coating at least partially prevents a fluid from interacting with the at least one sensor;

measuring initial characteristics associated with at least one barrier coating associated with at least one corresponding sensor responsive to a plurality of fluids, the initial characteristics comprising an initial acoustic wave property and an initial optical property;

exposing each barrier coating to at least two of the plurality of fluids;

measuring subsequent characteristics associated with the at least one barrier coating, the subsequent characteristics comprising a subsequent acoustic wave property and a subsequent optical property;

wherein the initial and subsequent acoustic wave properties correlate to the density, viscosity, mass, or crytallinity of the sensor material before and after, respectively, exposure of the coating to the plurality of fluids, and the initial and subsequent optical properties correspond to the ability of the sensor to respond to radiation before and after, respectively, exposure of the coating to the plurality of fluids;

determining a first barrier property and a second barrier property associated with the at least one barrier coating with respect to at least two of the plurality of fluids based on the initial characteristics and subsequent characteristics.

29. The method of claim 28, where the initial characteristics are measured prior to the exposure to the fluids and the subsequent characteristics are measured subsequent to exposure to the fluids.

30. The method of claim 28, where the measurement of the initial acoustic wave property and the measurement of the subsequent acoustic wave property each further comprises:

inducing an oscillation in the sensor; and
measuring the acoustic wave property.

31. The method of 28, where the measurement of the initial optical property and the measurement of the subsequent optical property each further comprises:

delivering a reference radiation toward the sensor and the associated barrier coating; and
measuring a resulting radiation.

32. The method of claim 28, where the initial optical property and subsequent optical property associated with each barrier coating are selected from the group consisting of absorbance, luminescence, refractive index, scattering, and a combination thereof.

33. The method of claim 28, where the sensor comprises a total-internal reflection element, and wherein the initial optical property and the subsequent optical property associated with each barrier coating are determined from radiation propagated within the total-internal reflection element.

34. The method of claim 28, where the barrier coating comprises a material selected from the group consisting of an organic material, a polymer with additives, an organic-inorganic hybrids, a polycarbonate, polycarbonate blends, polycarbonate-polyorganosiloxane copolymers, polyetherimide resins, oxides, nitrides and oxinitrides of silicon, aluminum, zinc, boron and other metals, ceramics, polyvinyl alcohol, ethylene vinyl alcohol copolymers, polyvinyl dichloride, nylon, cellophane, polypropylene, paphen phenoxy resin, high density polyethylene, low density polyethylene, poly (vinyl chloride), polyacetal, polystyrene, polyvinyl acetate, poly (butylene terphthalate), poly (ethylene terphthalate), poly (ethylene naphthalate), poly (vinylidene chloride), and combinations thereof.

35. The method of claim 28, where the sensor comprises a sensing layer.

36. The method of claim 35, where the sensing layer comprises a material that does not change the properties of the coating layer and that interacts with the plurality of fluids in a manner that may be measured.

37. The method of claim 35, where the sensing layer comprises a luminophore or colorimetric reagent.

38. The method of claim 28, where the plurality of fluids are selected from the group consisting of oxygen; water vapor; ammonia; carbon dioxide; carbon monoxide; ethylene oxide; helium; hydrogen; hydrogen sulfide; methyl bromide; nitrogen; sulfur dioxide; fuels; alkaline and acidic solutions; water; organic solvents of different polarity; solvent mixtures; gasoline; mixtures containing hexane; a hexane/toluene mixture; ketones; glycol ethers; glycol ether esters; toluene; methylethyl ketone (MEK); ester solvents, butyl acetate, propyl acetate; alcohols; 1-methdyl-2-pyrrolidinone; xylenes; and a volatile inert solvent; and combinations thereof.

39. The method of claim 28, wherein the first barrier property corresponds to one of the two of the plurality of fluids based on the variation between the initial optical property and subsequent optical property associated with each barrier coating.

40. The method of claim 39, where the second barrier property corresponds to the other of the two of the plurality of fluids based on the variation between the initial acoustic wave property and subsequent acoustic wave property associated with each barrier coating.

41. The method of claim 28, where measuring of the initial optical property and the corresponding initial acoustic wave property occurs simultaneously.

42. The method of claim 28, where measuring of the subsequent optical property and the corresponding subsequent acoustic wave property of each barrier coating occurs simultaneously.

43. The method of claim 28, where the at least one sensor further comprises a plurality of substrates; and where the at least one barrier coating comprises a plurality of barrier coatings, where the plurality of barrier coatings comprise a combinatorial array.

44. The method of claim 43, further comprising determining the relative performance of each of the first barrier property and second barrier property for each of the plurality of barrier coatings.

45. A method for screening for barrier properties of a barrier coating, comprising:
- positioning at least one barrier coating between a plurality of fluids and at least one sensor wherein said sensor comprises at least one material responsive to interactions with a plurality of fluids, and wherein said barrier coating at least partially prevents a fluid from interacting with the at least one sensor;
- measuring initial characteristics associated with at least one barrier coating associated with at least one corresponding sensor responsive to a plurality of fluids, the initial characteristics comprising an initial acoustic wave property and an initial optical property;
- exposing each barrier coating to at least two of the plurality of fluids;
- simultaneously measuring subsequent characteristics associated with the at least one barrier coating, the subsequent characteristics comprising a subsequent acoustic wave property and a subsequent optical property;
- wherein the initial and subsequent acoustic wave properties correlate to the density, viscosity, mass, or crytallinity of the sensor material before and after, respectively, exposure of the coating to the plurality of fluids, and the initial and subsequent optical properties correspond to the ability of the sensor to respond to radiation before and after, respectively, exposure of the coating to the plurality of fluids;
- determining a first barrier property and a second barrier property associated with the at least one barrier coating with respect to at least two of the plurality of fluids based on the initial characteristics and subsequent characteristics, where the initial characteristics are measured prior to the exposure to the fluids and the subsequent characteristics are measured subsequent to exposure to the fluids.

46. The method of claim 45, where the measurement of the initial acoustic wave property and the measurement of the subsequent acoustic wave property each further comprises:
- inducing an oscillation in the sensor; and
- measuring the acoustic wave property.

47. The method of 45, where the measurement of the initial optical property and the measurement of the subsequent optical property each further comprises:
- delivering a reference radiation toward the sensor associated with the at least one barrier coating; and
- measuring a resulting radiation.

48. The method of claim 47, wherein the initial optical property or the subsequent optical property is based, respectively, on a reference radiation or a resulting radiation having an intensity in the range of about a single photon to about 1 kilowatt.

49. The method of claim 47, wherein the initial optical property or the subsequent optical property is based, respectively, on a reference radiation or a resulting radiation having a wavelength in the range of about 10 nanometers to about 50 micrometers.

50. The method of claim 47, wherein the initial optical property or the subsequent optical property is based, respectively, on a reference radiation or a resulting radiation having a polarization state in the range of about 0 degrees to about 360 degrees.

51. The method of claim 47, wherein the initial optical property or the subsequent optical property is based, respectively, on a reference radiation or a resulting radiation having a phase difference in the range of about 0.001 to about 10,000 wavelengths of probe radiation.

52. The method of claim 47, wherein the initial optical property or the subsequent optical property is based, respectively, on a reference radiation or a resulting radiation having a luminescence lifetime in the range of about 10 picoseconds–1000 seconds.

53. The method of claim 47, wherein the initial optical property or the subsequent optical property is based, respectively, on a reference radiation or a resulting radiation having a time delay in the range of about 1 femtosecond–1000 seconds.

54. The method of claim 45, where the initial optical property and subsequent optical property associated with each barrier coating are selected from the group consisting of absorbance, luminescence, refractive index, scattering, and a combination thereof.

55. The method of claim 45, where the sensor comprises a total-internal reflection element, and wherein the initial optical property and the subsequent optical property associated with each barrier coating are determined from radiation propagated within the total-internal reflection element.

56. The method of claim 45, wherein the first barrier property corresponds to one of the two of the plurality of fluids based on the variation between the initial optical property and subsequent optical property of each barrier coating.

57. The method of claim 45, where the second barrier property corresponds to the other of the two of the plurality of fluids based on the variation between the initial acoustic wave property and subsequent acoustic wave property of each barrier coating.

58. The system of claim 1, wherein the at least one barrier coating is deposited on the external surface of the at least one sensor.

59. The system of claim 1, further comprising:
- a gas-impermeable cell having an interior chamber, the at least one sensor positioned within the interior chamber; and
- a substrate attachable to the gas-impermeable cell so as to seal the interior chamber, wherein the at least one barrier coating is deposited on the substrate.

60. The system of claim 1, further comprising:
- a gas-impermeable cell having an interior chamber, the at least one optical sensor with a total-internal reflection element as a transducer positioned within the interior chamber; and
- a substrate attachable to the gas-impermeable cell so as to seal the interior chamber, wherein the at least one barrier coating is deposited on the substrate.

61. A system for determining barrier properties of a barrier coating, comprising:
- at least one dual-mode transducer comprising at least one sensor having at least one external surface, the at least one sensor comprising at least one material responsive to interactions with a plurality of fluids;

a gas-impermeable cell having an interior chamber, the at least one sensor positioned within the interior chamber;

at least one barrier coating associated with each sensor, such that said barrier coating is positioned between said sensor and said fluids to thereby modify the interaction of said sensor with said fluids, and wherein said barrier coating at least partially prevents a fluid from interacting with said at least one sensor, with each sensor having initial characteristics and subsequent characteristics each associated with the barrier properties of the coating with respect to each of a plurality of fluids, where the initial characteristics correspond to the barrier coating properties prior to exposure to any of the plurality of fluids and the subsequent characteristics correspond to the barrier coating properties after exposure to at least two of a plurality of fluids, with the initial characteristics for each barrier coating comprising an initial optical property and an initial acoustic wave property, and the subsequent characteristics of each barrier coating comprising a subsequent optical property and subsequent acoustic wave property;

wherein the initial and subsequent acoustic wave properties correlate to the density, viscosity, mass, or crytallinity of the sensor material before and after, respectively, exposure of the coating to the plurality of fluids, and the initial and subsequent optical properties correspond to the ability of the sensor to respond to radiation before and after, respectively, exposure of the coating to the plurality of fluids;

a substrate attachable to the gas-impermeable cell so as to seal the interior chamber, wherein the at least one barrier coating is deposited on the substrate;

an optical characteristic measurement device for measuring the initial optical property and subsequent optical property associated with each barrier coating;

an acoustic wave property measurement device for measuring the initial acoustic wave property and the subsequent acoustic wave property associated with each barrier coating; and a computer for determining a first barrier property and a second barrier property of each barrier coating, the first barrier property with respect to one of the plurality of fluids, the second barrier property with respect to a second of the plurality of fluids, the first barrier property and the second barrier property based on the variation between the initial characteristics and subsequent characteristics associated with both the optical properties and the acoustic wave properties of each barrier coating.

* * * * *